United States Patent
Niederauer et al.

(10) Patent No.: US 10,702,686 B2
(45) Date of Patent: Jul. 7, 2020

(54) WOUND OXYGEN SUPPLY SYSTEM

(71) Applicant: Electrochemical Oxygen Concepts, Inc., San Antonio, TX (US)

(72) Inventors: Mark Q. Niederauer, San Antonio, TX (US); James P. Daley, San Antonio, TX (US); Joseph J. Moffett, Crownsville, MD (US)

(73) Assignee: Electrochemical Oxygen Concepts, Inc., San Antonio, TX (US)

( * ) Notice: Subject to any disclaimer, the term of this patent is extended or adjusted under 35 U.S.C. 154(b) by 301 days.

(21) Appl. No.: 15/639,845

(22) Filed: Jun. 30, 2017

(65) Prior Publication Data

US 2019/0001107 A1    Jan. 3, 2019

(51) Int. Cl.
*A61M 35/00* (2006.01)
*G06F 19/00* (2018.01)
*G16H 40/63* (2018.01)

(52) U.S. Cl.
CPC ......... *A61M 35/30* (2019.05); *G06F 19/3418* (2013.01); *G16H 40/63* (2018.01);
(Continued)

(58) Field of Classification Search
CPC .......... A61M 35/00; A61M 2202/0208; A61M 16/16; A61M 16/161; A61M 2205/8206; A61M 2205/52; A61M 2205/50; A61M 2205/505; A61M 2205/3331; A61M 2205/3334; A61M 2205/3368; A61M 2205/3584; A61M 2205/581;
(Continued)

(56) References Cited

U.S. PATENT DOCUMENTS

| 3,489,670 A | 1/1970 | Maget |
| 5,578,022 A | 11/1996 | Scherson et al. |

(Continued)

FOREIGN PATENT DOCUMENTS

| JP | 2000-507459 | 6/2000 |
| JP | 2002-524109 | 8/2002 |

(Continued)

OTHER PUBLICATIONS

International Search Report and Written Opinion dated Sep. 13, 2018 issued in corresponding PCT Patent App. No. PCT/US2018/38733 (13 pages).

(Continued)

*Primary Examiner* — Bhisma Mehta
*Assistant Examiner* — James D Ponton
(74) *Attorney, Agent, or Firm* — William B. Nash; Joseph R. Mencher; Haynes and Boone, LLP

(57) ABSTRACT

A wound oxygen supply system includes a chassis that defines an oxygen outlet. an oxygen production subsystem is included in the chassis and coupled to the oxygen outlet. A control subsystem is coupled to the oxygen production subsystem and configured to receive humidity information that is indicative of a humidity experienced by the oxygen production subsystem. The control system then uses the humidity information to control power provided to the oxygen production subsystem in order to control an oxygen flow that is created by the oxygen production subsystem and provided through the oxygen outlet to a restricted airflow enclosure adjacent a wound site.

20 Claims, 21 Drawing Sheets

(52) U.S. Cl.
CPC ............... *A61M 2202/0208* (2013.01); *A61M 2205/3331* (2013.01); *A61M 2205/3334* (2013.01); *A61M 2205/3368* (2013.01); *A61M 2205/3379* (2013.01); *A61M 2205/3382* (2013.01); *A61M 2205/3584* (2013.01); *A61M 2205/50* (2013.01); *A61M 2205/505* (2013.01); *A61M 2205/52* (2013.01); *A61M 2205/581* (2013.01); *A61M 2205/8206* (2013.01)

(58) Field of Classification Search
CPC .. A61M 2205/3382; A61M 2205/3379; A61M 35/30; G06F 19/341; G06F 19/3418; G16H 40/63
See application file for complete search history.

(56) References Cited

U.S. PATENT DOCUMENTS

| | | |
|---|---|---|
| 5,788,682 A | 8/1998 | Maget |
| 6,010,317 A | 1/2000 | Maget et al. |
| 6,071,267 A | 6/2000 | Zamierowski |
| 6,171,368 B1 | 1/2001 | Maget et al. |
| 7,014,630 B2 | 3/2006 | Rosati |
| 7,263,814 B2 | 9/2007 | Rosati |
| 7,316,857 B1 | 1/2008 | Swanson et al. |
| 7,322,971 B2 | 1/2008 | Shehada |
| 7,368,005 B2 | 5/2008 | Bliss et al. |
| 10,226,610 B2 * | 3/2019 | Wells .................... A61M 35/00 |
| 2003/0083610 A1 | 5/2003 | McGrath et al. |
| 2006/0225737 A1 | 10/2006 | Iobbi |
| 2006/0287632 A1 | 12/2006 | Sarangapani |
| 2007/0299412 A1 | 12/2007 | Vogel |
| 2008/0003299 A1 | 1/2008 | Trotter et al. |
| 2008/0308100 A1 | 12/2008 | Pujol et al. |
| 2013/0144227 A1 | 6/2013 | Locke et al. |
| 2014/0273042 A1 * | 9/2014 | Saint .................. A61B 5/14532 435/14 |
| 2016/0082238 A1 * | 3/2016 | Wells .................... A61M 35/00 604/24 |

FOREIGN PATENT DOCUMENTS

| | | |
|---|---|---|
| JP | 2004-529090 | 9/2004 |
| JP | 2005-511205 | 4/2005 |
| JP | 2008-539966 | 11/2008 |
| WO | WO 2006/122169 | 11/2006 |

OTHER PUBLICATIONS

Search Report issued from Japan Patent Office (and English translation) in Japanese Patent Application 2011-533156, dated Jun. 25, 2013, 9 pages.

International Search Report and Written Opinion dated Feb. 24, 2017 issued in co-pending PCT Application Serial No. PCT/US16/65378 (18 pages).

* cited by examiner

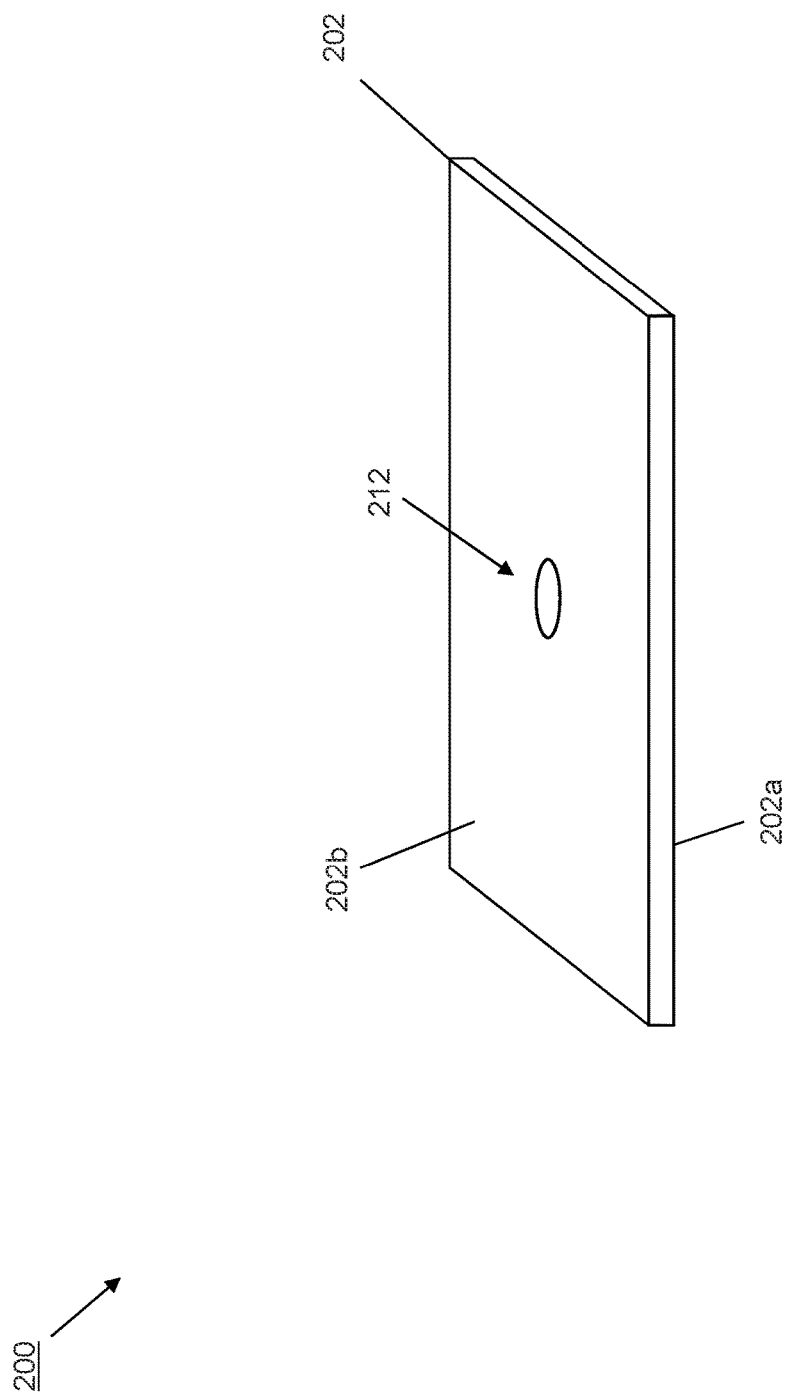

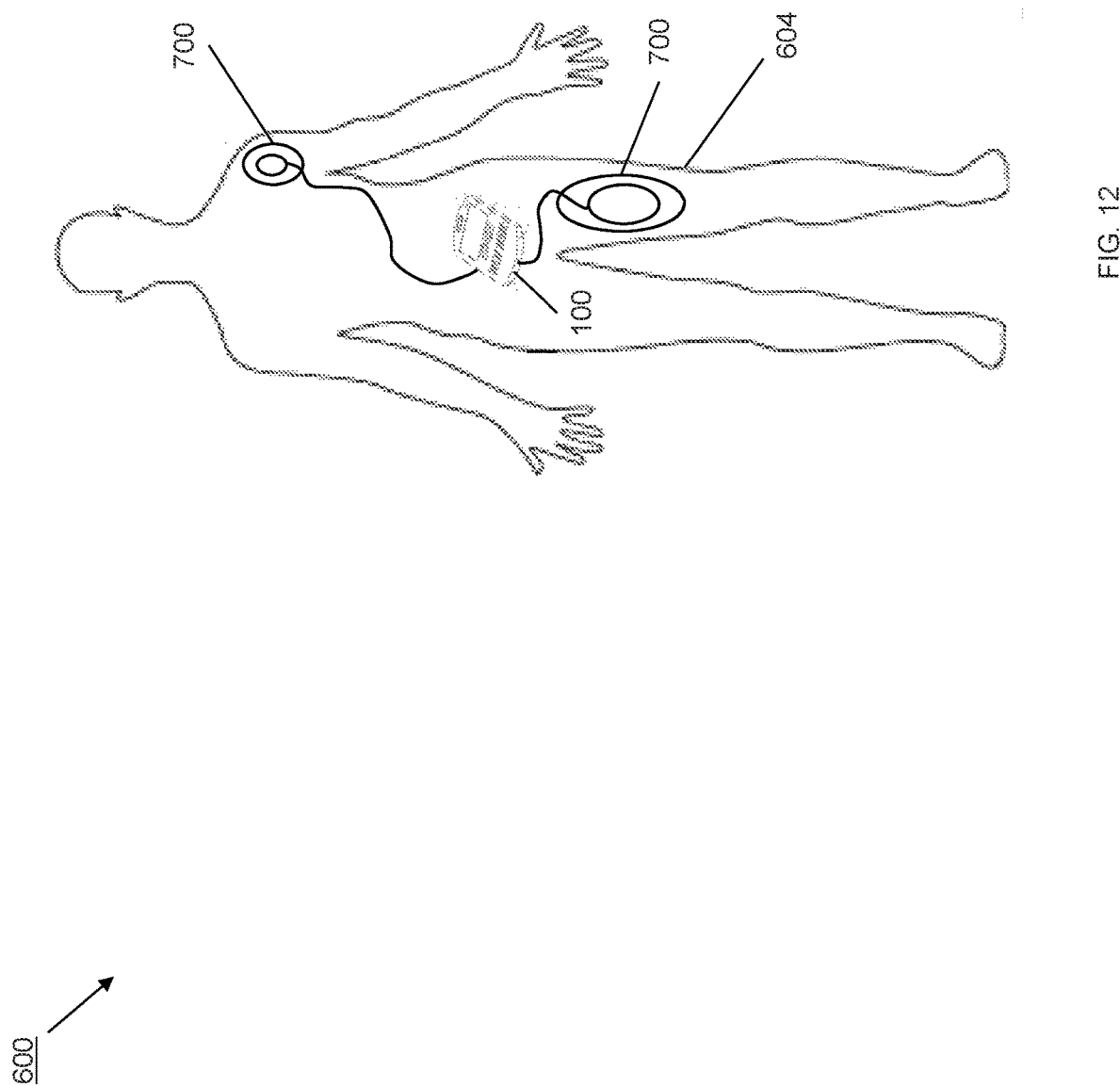

WOUND OXYGEN SUPPLY SYSTEM

BACKGROUND

The present disclosure relates generally to wound healing, and more particularly to systems and methods for supplying oxygen to a wound to accelerate the healing of damaged tissue and/or promote tissue viability.

When tissue is damaged and a wound results, a four phase healing process begins, and optimal metabolic function of cells in the tissue to repopulate the wound requires that oxygen be available for all of these phases of wound healing. Furthermore, the more layers of tissue that are damaged, the greater the risk is for complications to occur in the wound healing process, and difficult-to-heal wounds can encounter barriers to the wound healing process and experience delays in one or more of the last three phases of wound healing. For example, one of the most common contributing factors to delays in the healing of wounds such as venous leg ulcers, diabetic foot ulcers, and pressure ulcers, is the problem of chronic wound ischemia. Chronic wound ischemia a pathological condition that restricts blood supply, oxygen delivery, and blood request for adequate oxygenation of tissue, which inhibits normal wound healing.

One conventional standard of care for treating difficult-to-heal wounds involves the use of an advanced wound dressing, or a combination of advanced wound dressings, that provide a dressing treatment system. The advanced wound dressing may be positioned on the wound site and, in some cases, the surrounding intact skin, to provide a wound site enclosure. The advanced wound dressing typically includes materials having properties for promoting moist wound healing, managing wound exudate, and helping control wound bioburden. Those material provided in combination operate to produce limited moisture vapor permeability, and the more occlusive the dressing, the lower the amount of ambient air (and thus a respective lower amount of oxygen) that is available to the wound site.

100% oxygen exerts a partial pressure of 760 millimeters (mm) of mercury (Hg), and ambient air includes about 21% oxygen, so ambient air exerts a partial pressure of oxygen of about 159 mm Hg. A typical advanced wound dressing or wound dressing system utilizing materials that provide limited moisture vapor permeable operates to impacts the available oxygen for the wound site, thereby limiting the partial pressure of oxygen at the enclosed wounds site to about 10-60 mm Hg. Fresh air (and its associated higher oxygen amount) is then only provided to the wound site when the dressing is changed, and dressings may remain covering the wound site for up to seven days before a dressing change is required. As such, the limited moisture vapor permeability of advanced wound dressings produce a reduced oxygen wound environment that works against the optimal metabolic function of cells to repopulate the wound during all the phases of wound healing.

Specific examples of conventional systems and methods to provide tissue oxygenation for difficult-to-heal wounds include the intermittent or continuous application of topical hyperbaric oxygen to the wound site. Intermittent topical hyperbaric oxygen treatment systems involve providing a sealed extremity or partial body chamber, along with a connected source of pure oxygen at a relatively high flow rate, and positioning the wounded limb or body area in the sealed extremity chamber or partial body chamber. The oxygen source will then supply the chamber with up to 100% oxygen at flow rates that may exceed 300 liters per hour, pressurizing the interior of the chamber at up to 1.05% normal atmospheric pressure, thereby topically increasing the available oxygen for cellular processing at the affected wound site. For example, during oxygen application, the partial pressure of oxygen exerted inside the sealed extremity or partial body chamber may attain 798 mm Hg, and may be applied for about 90 minutes. These and similar methods of applying intermittent topical hyperbaric oxygen are restrictive, cumbersome, can only supply oxygen to the affected area intermittently with no systemic application, and only provide for a minimal increase in atmospheric pressure (about 5%). Therefore, the effects of the oxygen therapy on wounds using these methods tend to be minimal, which is evidenced by the lack of commercial success of topical hyperbaric oxygen extremity chambers.

Other conventional systems and methods to provide tissue oxygenation include disposable devices that provide for the transmission of gases in ionic form through ion-specific membranes in order to apply supplemental oxygen directly to a wound site. These devices are typically battery powered, disposable, oxygen supplemented bandages that are provided directly over the wound site, and utilize electrochemical oxygen generation using variations of a 4 electron formula originally developed for NASA. In such systems, the amount of oxygen that can be applied to the wound is typically in the range of 3 to 15 milliliters per hour, and desired oxygen flow rates are generated by utilizing corresponding, preselected battery sizes with predefined amperages. As such, these devices are either "on or off", and do not have the ability to deliver a varying or adjustable oxygen flow or oxygen flow rate without obtaining a new device and/or a different battery having an amperage that will produce the desired flow rate. The utilization of fixed, non-variable oxygen flows and oxygen flow rates introduces corresponding limitations in the treatment of different sizes and types of wounds, and tends to result in the wound treatment system being oversized or undersized for the wound to which it is being applied.

The inventors of the present disclosure co-invented systems and methods that address the issues with the conventional wound treatment systems discussed above. For example, U.S. Pat. No. 8,287,506 and U.S. Patent Publication No. 2016/0082238 describe wound treatment systems that provide for low dose tissue oxygenation and continuous oxygen adjustability to wound site(s) to create a controlled hyperoxia and hypoxia wound environment for damaged tissue, accelerates wound healing, and promotes tissue viability. Those systems and methods operate by monitoring pressure information that is indicative of a pressure in a restricted airflow enclosure that is located adjacent a wound site (e.g., provided by a wound dressing), and using the pressure information to control power provided to an oxygen production subsystem in order to control an oxygen flow that is created by the oxygen production subsystem and provided to the restricted airflow enclosure. In some embodiments, those wound treatment systems include a flow sensor that measures the oxygen output of the oxygen production subsystem, with a pressure sensor downstream of the flow sensor that measures the pressure that may be utilized to control the oxygen flow created by the oxygen production subsystem as discussed above.

However, the inventors of the present disclosure have discovered that such wound treatment systems suffer from a number of issues. For example, the flow sensor utilized with such wound treatment systems is relatively large (currently approximately 36 mm by 20 mm), relatively expensive (currently approximately $60 USD), consumes a relatively high amount of energy (up to 40 milliamps (ma)), and requires "plumbing" (i.e., tubing that connects the flow sensor to the oxygen flow(s) that it measures) that takes up space in the wound treatment system chassis and results in a larger chassis than would otherwise be required absent the flow sensor. Furthermore, it has been discovered that oxygen production subsystem utilized with such wound treatment systems may provide greatly reduced oxygen production as humidity decreases, which can result in deficient wound site oxygen supply, and can cause the wound treatment systems to increase the power provided to the oxygen production subsystem to a level that can damage the oxygen production subsystem.

Accordingly, it would be desirable to provide an improved wound treatment system.

SUMMARY

According to one embodiment, a wound oxygen supply system includes a processing system; and a memory system that is coupled to the processing system and that includes instructions that, when executed by the processing system, cause the processing system to perform operations including: receiving humidity information that is indicative of a humidity experienced by an oxygen production subsystem; and controlling, using the humidity information, power provided to the oxygen production subsystem in order to control an oxygen flow that is created by the oxygen production subsystem and provided to a restricted airflow enclosure.

BRIEF DESCRIPTION OF THE DRAWINGS

FIG. 2C is a bottom perspective view illustrating an embodiment of the wound oxygen supply system of FIG. 2A

FIG. 12 is a schematic view illustrating an embodiment of the patient of FIG. 6 with additional wounds, and utilizing the wound oxygen supply system of FIG. 1 and multiple bandage subsystems of FIG. 7A-7D.

DETAILED DESCRIPTION

Some embodiments of wound oxygen supply systems and methods will now be described with reference to the figures, but one of skill in the art in possession of the present disclosure will recognize that a wide variety of modification to those embodiments will fall within the scope of the present disclosure as well. As such, different combinations of the different components and configurations of the wound oxygen supply systems discussed below, substitutions of different components in different wound oxygen supply systems, and/or any other modifications that would be apparent to one of skill in the art in possession of the present disclosure are envisioned as falling within the scope of the present disclosure.

Figure 1A:
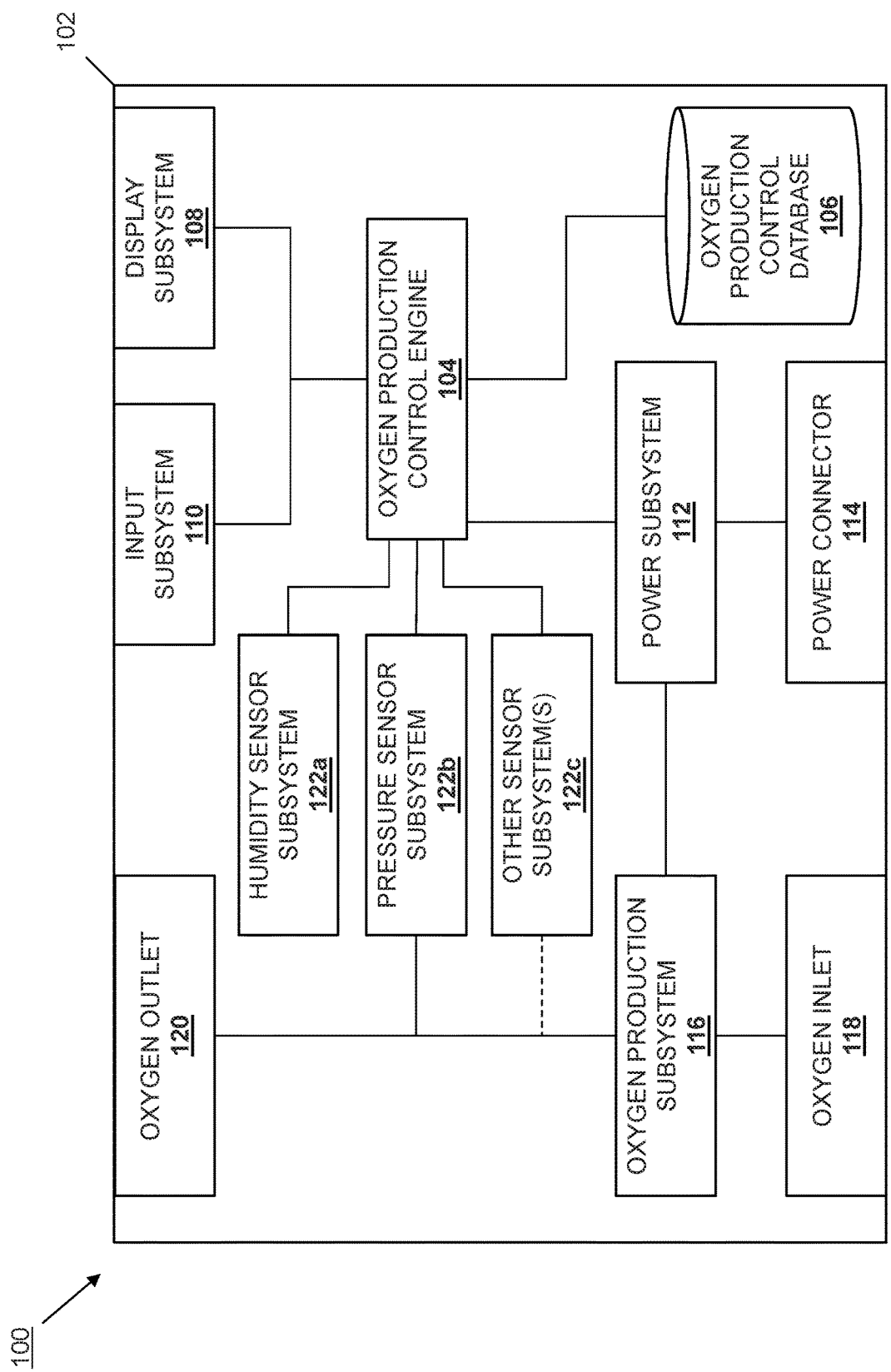
FIG. 1A is a schematic view illustrating an embodiment of a wound oxygen supply system.
Figure 1B:
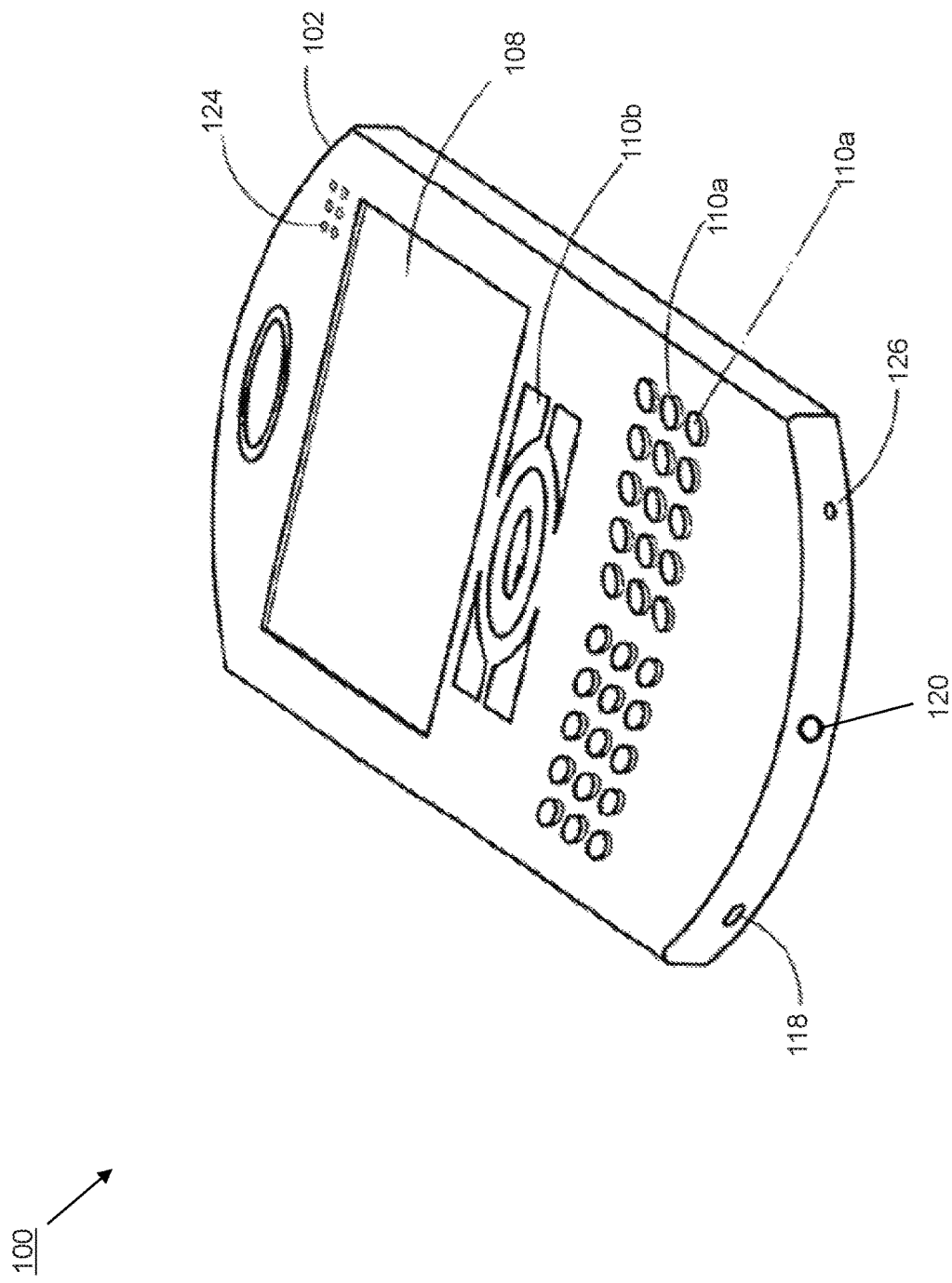
FIG. 1B is a perspective view illustrating an embodiment of the wound oxygen supply system of FIG. 1A.

Referring now to FIGS. 1A and 1B, an embodiment of a wound oxygen supply system 100 is illustrated. The wound oxygen supply system 100 illustrated in FIGS. 1A and 1B provides an example of an wound treatment device that includes the oxygen production subsystems, sensor subsystems, power subsystems, and control subsystems in a single chassis that may be coupled to oxygen delivery tubing that is further coupled to a bandage subsystem. In the illustrated embodiment, the wound oxygen supply system 100 includes a chassis 102 that houses the components of the wound oxygen supply system 100, only some of which are illustrated in FIG. 1A. For example, the chassis 102 may house a processing subsystem (not illustrated, but which may include one or more hardware processors known in the art) and a memory subsystem (not illustrated, but which may include one or more memory devices known in the art) that includes instructions that, when executed by the processing subsystem, cause the processing subsystem to provide an oxygen production control engine 104 that is configured to perform the functions of the oxygen production control engines and wound oxygen supply systems discussed below. The chassis 102 may also house a storage subsystem (not illustrated, but which may include one or more storage devices known in the art) that is coupled to the oxygen production control engine 104 (e.g., via a coupling between the storage subsystem and the processing subsystem) and that stores an oxygen production control database 106 that may include any of the information utilized to provide the functionality discussed below.

The chassis 102 may also house and/or include a display subsystem 108 that is coupled to the oxygen production control engine 104 (e.g., via a coupling between the display subsystem 108 and the processing subsystem) and that is configured to display any of the information discussed below. The chassis 102 may also house an input subsystem 110 that is coupled to the oxygen production control engine 104 (e.g., via a coupling between the input subsystem 110 and the processing subsystem) and that is configured to receive and provide any of the input information (e.g., via the input buttons 110a and 110b illustrated in FIG. 1B) to the oxygen production control engine 104 as discussed below. While the display subsystem 108 and the input subsystem 110 are illustrated and described as separate subsystems, one of skill in the art in possession of the present disclosure will recognized that they may be combined (e.g., in a touch-input display subsystem) while remaining within the scope of the present disclosure. The chassis 102 may also house a power subsystem 112 that is coupled to the oxygen production control engine 104 (e.g., via a coupling between the power subsystem 112 and the processing subsystem) and that may include one or more batteries, adapters, converters, and/or a variety of other power components that would be apparent to one of skill in the art in possession of the present disclosure. For example, in some of the specific examples discussed below, the power subsystem 112 includes a rechargeable battery and is coupled to a power connector 114 that is configured to connect to a power source to provide power to the power subsystem 112 to charge the rechargeable battery. However, one of skill in the art in possession of the present disclosure will recognize that direct power source systems (e.g., systems that connect to a power source outside the chassis 102 and thus do not require an internal battery or other stored power source to provide power, but that may be utilized in conjunction with internal batteries in some embodiments) may be provided while remaining within the scope of the present disclosure as well.

The chassis 102 also houses an oxygen production subsystem 116 that is coupled to the power subsystem 112 and that is configured to produce oxygen in response to power supplied by the power subsystem 112, as discussed in further detail below. The oxygen production subsystem 116 is coupled to an oxygen inlet 118 that is configured to direct ambient air that is adjacent the chassis 102 to the oxygen production subsystem 116, and an oxygen outlet 120 that is configured to direct an oxygen flow generated by the oxygen production subsystem 116 out of the chassis 102, as discussed below. For example, the chassis 102 and/or the oxygen outlet 120 may include a variety of fittings, connectors, and/or other couplings that provide for the attachments of tubing or a bandage subsystem to the chassis 102, discussed below. In a specific example, the oxygen outlet 120 may include a Leur-type locking fitting that is configured to engage tubing to maintain an airtight seal, although other couplings will fall within the scope of the present disclosure as well. While the oxygen outlet 120 is illustrated in FIG. 1B as a single oxygen outlet, the chassis 102 may define, and the oxygen production subsystem 116 may be coupled to, multiple oxygen outlets that are similar to the oxygen outlet 120 but that may be utilized to provide oxygen to different wounds on a patient, as discussed in further detail below. As such, each oxygen outlet may be coupled to the oxygen production subsystem 116, or an oxygen production subsystem that is substantially similar to the oxygen production subsystem 116 described herein, in order to allow for the treatment of multiple different wounds on a patient. In the illustrated embodiment, the chassis 102 houses a plurality of sensor subsystems, including a humidity sensor subsystem 122a, a pressure sensor subsystem 122a, and one or more other sensor subsystems 122c, discussed below. Furthermore, in embodiments in which multiple oxygen outlets provide oxygen from one or more oxygen production subsystems in the chassis 102, one or more sensor subsystems may be provided similarly as the sensors subsystems discussed below.

In an embodiment, the humidity sensor subsystem 122a is located in the chassis 102, coupled to the oxygen production control engine 104 (e.g., via a coupling between the humidity sensor subsystem 122a and the processing subsystem), and configured to monitor a humidity in the chassis 102 and provide humidity information that is indicative of a level of humidity in the chassis 102 to the oxygen production control engine 104. For example, the humidity sensor subsystem 122a may include an Si7007-A20 Relative Humidity (RH) sensor available from Silicon Labs of Austin, Tex., United States, as well as fittings, connectors, and/or other couplings for coupling that humidity sensor to the processing subsystem. As discussed in further detail below, such humidity sensors are relatively small (currently approximately 3 mm by 3 mm), relatively inexpensive (currently approximately $1.50 USD), and utilize a relatively simple coupling system to provide the functionality discussed below. However, while a specific humidity sensor subsystem has been described, one of skill in the art in possession of the present disclosure will recognize that humidity sensors may be provided in different locations (e.g., on a surface of the chassis 102 to measure the humidity outside of the chassis 102, coupled to the oxygen outlet 120 to measure a humidity in the restricted airflow enclosure, in or adjacent the restricted airflow enclosure, etc.) and/or otherwise utilized with the teachings of the present disclosure while remaining within its scope. Furthermore, while the embodiment illustrated in FIG. 1A includes a plurality of other sensor subsystems, as discussed below, in some situations the other sensors subsystems illustrated in FIG. 1A may be omitted and the humidity sensor subsystem may be the only sensor subsystem utilized in the wound oxygen supply system 100.

In an embodiment, the pressure sensor subsystem 122b is located in the chassis 102, coupled to the oxygen flow coupling between the oxygen production subsystem 116 and the oxygen outlet 120, coupled to the oxygen production control engine 104 (e.g., via a coupling between the pressure sensor subsystem 122b and the processing subsystem), and configured to monitor the pressure in the oxygen flow coupling between the oxygen production subsystem 116 and the oxygen outlet 120, and provide pressure information to the oxygen production control engine 104 that is indicative of a pressure in a restricted airflow enclosure that is coupled to the oxygen outlet 120, discussed in further detail below. For example, the pressure sensor subsystem 122b may include pressure sensor available from Honeywell International Inc. of Morris Plains, N.J., United States, as well as fittings, connectors, and/or other couplings for coupling that pressure sensor to the processing subsystem and the oxygen flow coupling.

In some embodiments, the pressure sensor subsystem 122b may measure pressure relative to atmospheric pressure, regardless of gas concentrations. However, in some embodiments, the pressure sensor subsystem 122b may include an oxygen partial pressure sensor subsystem that is configured to measure the oxygen partial pressure in the oxygen flow coupling between the oxygen production subsystem 116 and the oxygen outlet 120, and provide oxygen partial pressure information to the oxygen production control engine 104*a* that is indicative of an oxygen partial pressure in a restricted airflow enclosure that is coupled to the oxygen outlet 120, discussed in further detail below. However, while a specific pressure sensor subsystem has been described, one of skill in the art in possession of the present disclosure will recognize that pressure sensors may be provided in different locations (e.g., in the tubing coupled to the restricted airflow enclosure, in the restricted airflow enclosure itself (e.g., as part of the bandage subsystem discussed below, etc.), in or below the wound (i.e. or below the wound bed), and/or otherwise utilized with the teachings of the present disclosure while remaining within its scope. Furthermore, as discussed below, in some situations the pressure sensors subsystem illustrated in FIG. 1A may be omitted, and the humidity sensor subsystem may be the only sensor subsystem utilized in the wound oxygen supply system 100.

In an embodiment, the other sensor subsystems 122*c* may be located in the chassis 102, in some cases coupled to the oxygen flow coupling between the oxygen production subsystem 116 and the oxygen outlet 120, and coupled to the oxygen production control engine 104 (e.g., via a coupling between the other sensor subsystem 122*c* and the processing subsystem), and configured to perform a variety of sensor monitoring functionality. For example, a flow sensor subsystem may be configured to monitor the oxygen flow produced by the oxygen production subsystem 116 and provided through the oxygen flow coupling between the oxygen production subsystem 116 and the oxygen outlet 120, and provide flow information to the oxygen production control engine 104 that is indicative of an oxygen flow being produced by the oxygen production subsystem 116 and provided to a restricted airflow enclosure that is coupled to the oxygen outlet 120, discussed in further detail below. However, while a specific flow sensor subsystem has been described, one of skill in the art in possession of the present disclosure will recognize that flow sensors may be provided in different locations (e.g., in the tubing coupled to the restricted airflow enclosure) and/or otherwise utilized with the teachings of the present disclosure while remaining within its scope. Furthermore, as discussed below, in some situations the flow sensors subsystem illustrated in FIG. 1A may be omitted, and the humidity sensor subsystem may be the only sensor subsystem utilized in the wound oxygen supply system 100.

In another example, a temperature sensor subsystem may be configured to monitor a temperature in the coupling between the oxygen production subsystem 116 and the oxygen outlet 120, and provide temperature information to the oxygen production control engine 104 that is indicative of a temperature in a restricted airflow enclosure that is coupled to the oxygen outlet 120, discussed in further detail below. However, while a specific temperature sensor subsystem has been described, one of skill in the art in possession of the present disclosure will recognize that temperature sensors may be provided in different locations (e.g., in the tubing coupled to the restricted airflow enclosure, in the restricted airflow enclosure itself (e.g., as part of the bandage subsystem discussed below, etc.)) while remaining within the scope of the present disclosure. Furthermore, as discussed below, in some situations the temperature sensors subsystem illustrated in FIG. 1A may be omitted, and the humidity sensor subsystem may be the only sensor subsystem utilized in the wound oxygen supply system 100.

In another example, a pH sensor subsystem may be configured to monitor a pH in the coupling between the oxygen production subsystem 116 and the oxygen outlet 120, and provide pH information to the oxygen production control engine 104 that is indicative of a pH in a restricted airflow enclosure that is coupled to the oxygen outlet 120, discussed in further detail below. However, while a specific pH sensor subsystem has been described, one of skill in the art in possession of the present disclosure will recognize that pH sensors may be provided in different locations (e.g., in the tubing coupled to the restricted airflow enclosure, in the restricted airflow enclosure itself (e.g., as part of the bandage subsystem discussed below, etc.)) while remaining within the scope of the present disclosure. Furthermore, as discussed below, in some situations the pH sensors subsystem illustrated in FIG. 1A may be omitted, and the humidity sensor subsystem may be the only sensor subsystem utilized in the wound oxygen supply system 100.

In another example, a perfusion sensor subsystem may be coupled configured to monitor perfusion in the coupling between the oxygen production subsystem 116 and the oxygen outlet 120, and provide perfusion information to the oxygen production control engine 104 that is indicative of perfusion in a restricted airflow enclosure that is coupled to the oxygen outlet 120, discussed in further detail below. Perfusion information may include, for example, information that describes the measurement of oxygen content in relative or absolute terms such as molar concentration, saturation of hemoglobin, and/or a variety of other measurement characteristics that would be apparent to one of skill in the art in possession of the present disclosure. However, while a specific perfusion sensor subsystem has been described, one of skill in the art in possession of the present disclosure will recognize that perfusion sensors may be provided in different locations (e.g., in the tubing coupled to the restricted airflow enclosure, in the restricted airflow enclosure itself (e.g., as part of the bandage subsystem discussed below, etc.)) while remaining within the scope of the present disclosure. Furthermore, as discussed below, in some situations the perfusion sensor subsystem illustrated in FIG. 1A may be omitted, and the humidity sensor subsystem may be the only sensor subsystem utilized in the wound oxygen supply system 100. While a plurality of specific sensor subsystems have been described, one of skill in the art in possession of the present disclosure will recognize that a variety of other sensors may be utilized with the wound oxygen supply system 100 to provide the functionality discussed below while remaining within the scope of the present disclosure.

Furthermore, while a specific wound oxygen supply system 100 has been described, one of skill in the art in possession of the present disclosure will recognize that a variety of other features may be included on the wound oxygen supply system 100 while remaining within the scope of the present disclosure. For example, as illustrated in FIG. 1B, the wound oxygen supply system 100 may include a speaker and/or microphone system 124 that are coupled to the processing subsystem in the wound oxygen supply system 100 and that are configured to receive and emit audible information, an input connector 126 that is configured to connect external subsystems to the wound oxygen supply system 100 (e.g., the input connector may be the power connector 114 discussed above with reference to FIG. 1A, a computing device connector such as a Universal Serial Bus (USB) connector, a headphone connector, and/or other input connectors known in the art), wired and/or wireless communication subsystems (e.g., BLUETOOTH® subsystems, Near Field Communication (NFC) subsystems, WiFi communication subsystems (that provide for communication through a Local Area Network (LAN), the Internet, etc.), wired connector subsystems, etc.) that provide for the communication of data as described below, and/or a variety of other features that would be apparent to one of skill in the art in possession of the present disclosure. As such, the addition of other features and/or subsystems to the wound oxygen supply system 100 is envisioned as falling within the scope of the present disclosure as well.

Figure 2A:
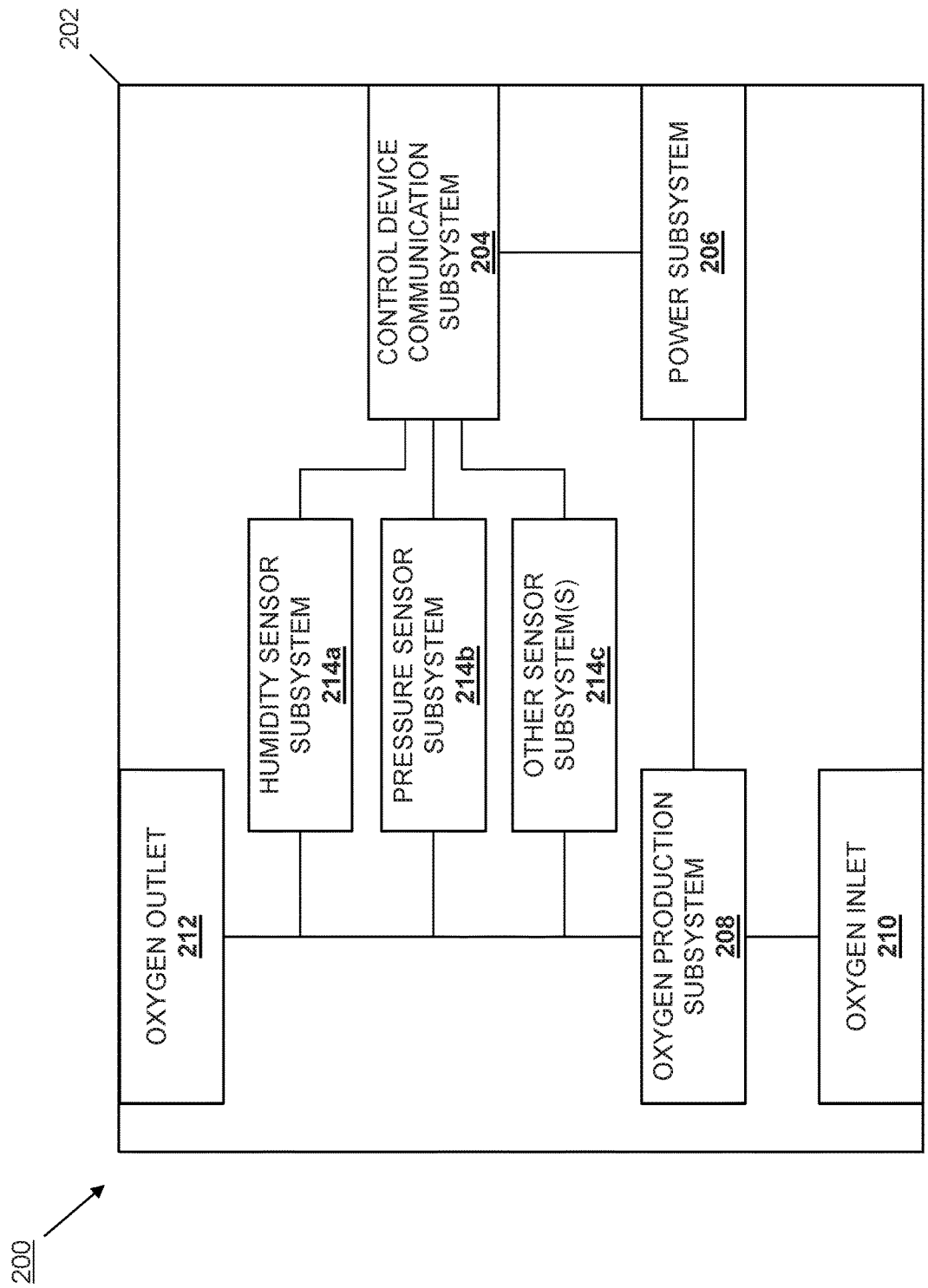
FIG. 2A is a schematic view illustrating an embodiment of a wound oxygen supply system.
Figure 2B:
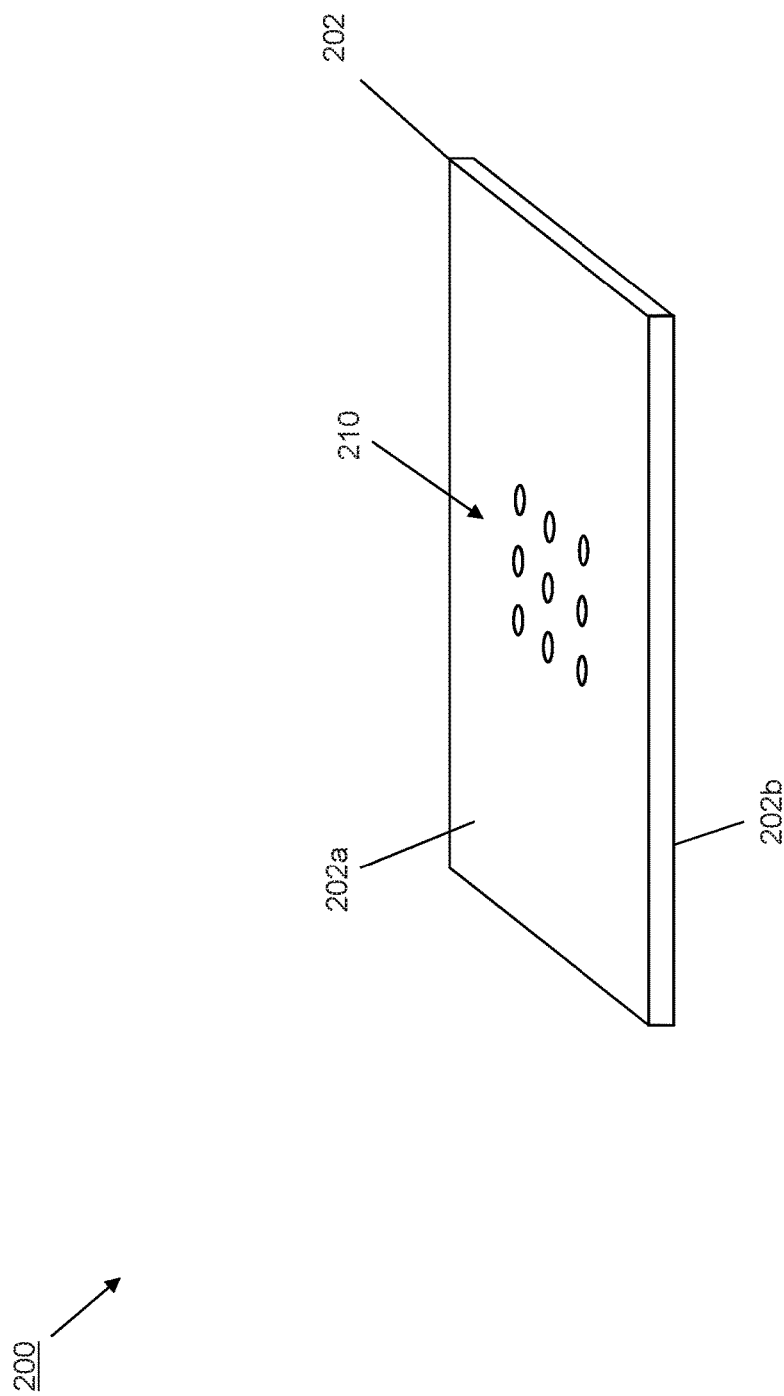
FIG. 2B is a top perspective view illustrating an embodiment of the wound oxygen supply system of FIG. 2A.

Referring now to FIGS. 2A, 2B, and 2C, another embodiment of a wound oxygen supply system 200 is illustrated. The wound oxygen supply system 200 illustrated in FIGS. 2A-2C provides an example of a wound treatment device that includes the oxygen production subsystems, sensor subsystems, and power subsystems in a single chassis that may be coupled to or integrated with a bandage subsystem, as well as a communication subsystem that may communicatively couple to a separate control device. In the illustrated embodiment, the wound oxygen supply system 200 includes a chassis 202 that houses the components of the wound oxygen supply system, only some of which are illustrated in FIG. 2A. For example, the chassis 202 may house a control device communication subsystem 204 that may include wired and/or wireless communication components (e.g., processing subsystems, memory subsystems, BLUETOOTH® subsystems, Near Field Communication (NFC) subsystems, WiFi communication subsystems (that provide for communication through a Local Area Network (LAN), the Internet, etc.), wired connector subsystems, etc.) that provide for the control device communication functionality discussed below.

The chassis 202 may also house a power subsystem 206 that is coupled to the control device communication subsystem 204 and that may include one or more batteries, adapters, converters, and/or a variety of other power components that would be apparent to one of skill in the art in possession of the present disclosure. For example, in some of the specific examples discussed below, the power subsystem 206 includes a rechargeable battery and may include a power connector (not illustrated, but which is similar to the power connector 114 discussed above with reference to FIGS. 1A and 1B), and that is configured to connect to a power source to provide power to the power subsystem 206 to charge the rechargeable battery. However, one of skill in the art in possession of the present disclosure will recognize that direct power source systems (e.g., systems that connect to a power source outside the chassis 202 and thus do not require an internal battery or other stored power source to provide power, but that may be utilized in conjunction with internal batteries as well), or external battery subsystems (discussed below) may be provided while remaining within the scope of the present disclosure as well.

The chassis 202 also houses an oxygen production subsystem 208 that is coupled to the power subsystem 206 and that is configured to produce oxygen in response to power supplied by the power subsystem 206 as discussed below. The oxygen production subsystem 208 is coupled to an oxygen inlet 210 that is configured to direct ambient air that is adjacent the chassis 202 to the oxygen production subsystem 208, and an oxygen outlet 212 that is configured to direct an oxygen flow generated by the oxygen production subsystem 208 out of the chassis 202, as discussed below. For example, the chassis 202 and/or the oxygen outlet 212 may include a variety of fittings, connectors, and/or other couplings that provide for the attachments of a bandage subsystem to the chassis 202, discussed below. With reference to FIGS. 2B and 2C, the chassis 202 is illustrated having a top surface 202a and a bottom surface 202b that is located opposite the chassis 202 from (and faces an opposite direction than) the top surface 202a. As illustrated, the chassis 102 defines a plurality of apertures that extend to the top surface 202a and provide the oxygen inlet 210, as well as defines an aperture that extends to the bottom surface 202b and provides the oxygen outlet 212. The embodiment of the wound oxygen supply system 200 illustrated in FIGS. 2B and 2C provides an example of one form factor that may be provided using the teachings of the present disclosure, particularly when utilizing the smaller form factor sensor subsystems (e.g., the humidity sensor subsystem discussed below) and omitting the larger form factor sensor subsystems (e.g., the flow sensor subsystem discussed below.) However, one of skill in the art in possession of the present disclosure will recognize that other form factors for the chassis 202 of the wound oxygen supply system 200, and other configurations of the oxygen inlet 210 and oxygen outlet 212, will fall within the scope of the present disclosure as well.

In the illustrated embodiment, the chassis 202 houses a plurality of sensor subsystems, including a humidity sensor subsystem 214a that may be substantially similar to the humidity sensor subsystem 122a discussed above with reference to FIG. 1A, a pressure sensor subsystem 214b that may be substantially similar to the pressure sensor subsystem 122b discussed above with reference to FIG. 1A, and one or more other sensor subsystems 214c that may be substantially similar to the other sensor subsystems 122c discussed above with reference to FIG. 1A. While a specific wound oxygen supply system 200 has been described, one of skill in the art in possession of the present disclosure will recognize that a variety of other features may be included on the wound oxygen supply system 200 while remaining within the scope of the present disclosure, and thus the additional of other features and/or subsystems to the wound oxygen supply system 200 is envisioned as falling within the scope of the present disclosure as well.

Figure 3A:
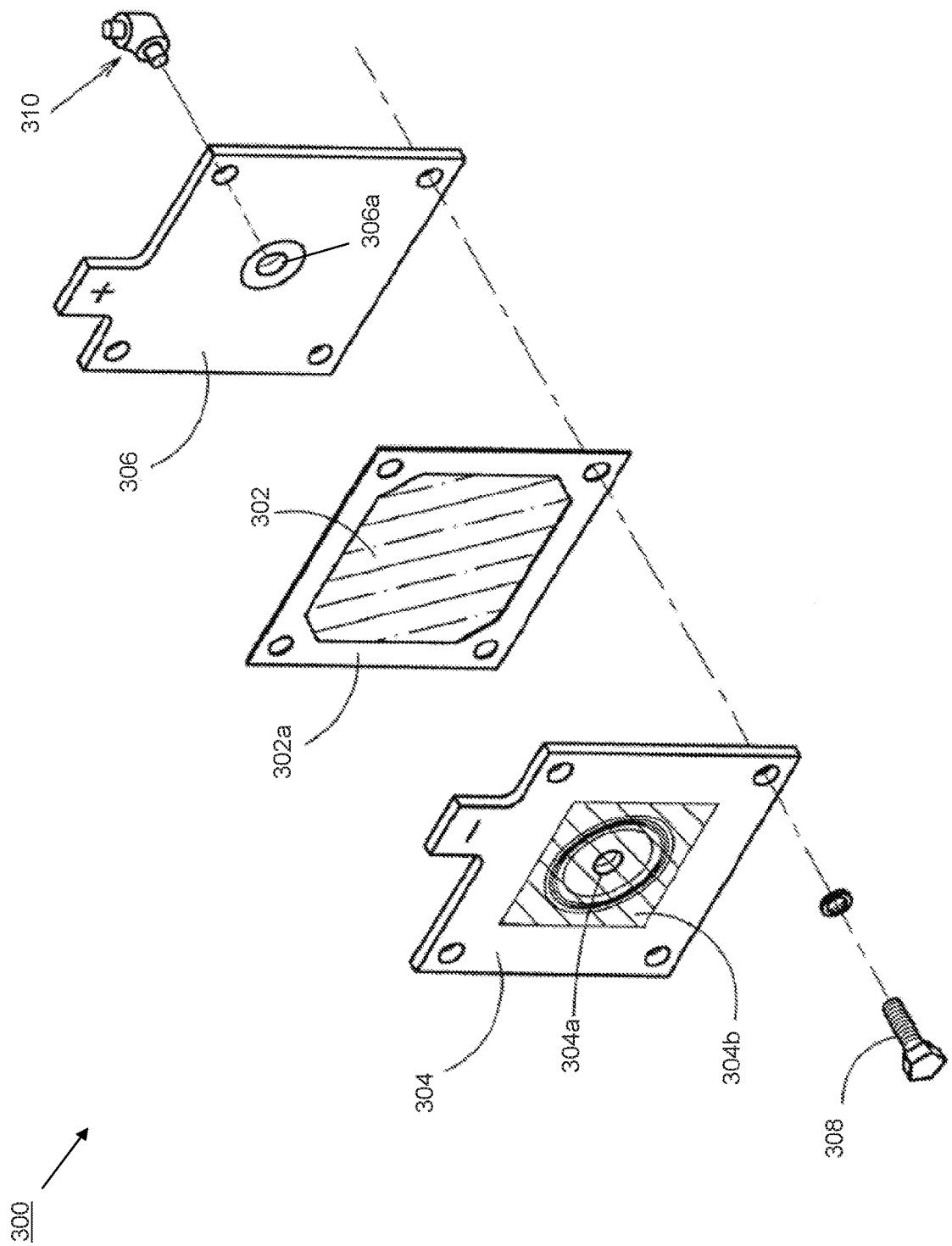
FIG. 3A is an exploded perspective view illustrating an embodiment of an oxygen production subsystem used in the wound oxygen supply systems of FIGS. 1A-1B and 2A-2C.
Figure 3B:
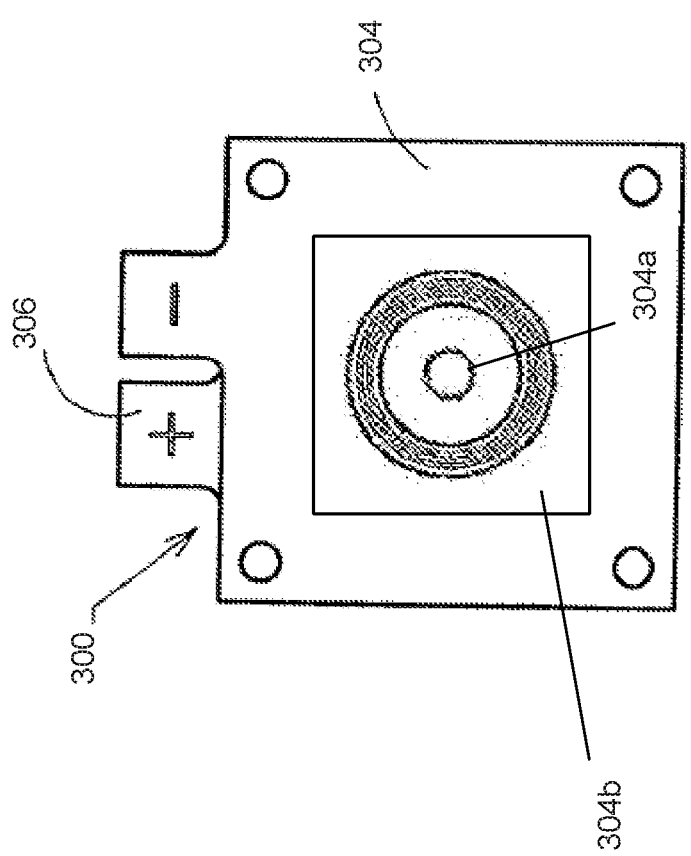
FIG. 3B is a front view illustrating an embodiment of the oxygen production subsystem of FIG. 3A.
Figure 3C:
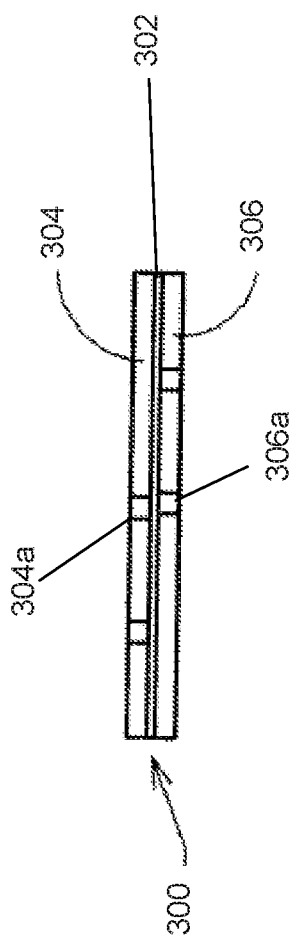
FIG. 3c is a cross sectional view illustrating an embodiment of the oxygen production subsystem of FIG. 3B.

Referring now to FIGS. 3A, 3B, and 3C, an embodiment of an oxygen production subsystem 300 is illustrated that may be the oxygen production subsystems 116 and/or 208, discussed above. In the illustrated embodiment, the oxygen production subsystem 300 is provided by an electrochemical oxygen generator/ion exchange oxygen concentrator, although other oxygen production subsystems will fall within the scope of the present disclosure as well. The oxygen production subsystem 300 in the illustrated embodiment includes a Proton Exchange Membrane (PEM) 302 that is located between a cathode plate 304 and an anode plate 306. In an embodiment, the PEM 302 may include a NAFION® oxygen transfer membrane as a proton conductor for the PEM 302, which may utilize a sulfonated tetrafluoroethylene copolymer, and which is available from DUPONT® of Wilmington, Del., United States. However, other PEMs and PEM materials may be utilized while remaining within the scope of the present disclosure as well. In the illustrated embodiment, the PEM 302 includes a gasket 302a that seals the PEM 302 between the cathode plate 304 and the anode plate 306. In an embodiment, the PEM 302 is compressed fully (e.g., utilizing approximately 3 to 6 Newton-meters (N-m) of force) between the cathode plate 304 and the anode plate 306, with the gasket 302a sealed utilizing a flange bolting subsystem 308. The cathode plate 304 defines an air inlet 304a that may be covered by a polarized membrane 304b that is configured to allow water vapor to pass in only one direction, and to maintain the encapsulation of other gases (e.g., hydrogen). In an embodiment, the polarized membrane 304b may be provided by a GORE-TEX® fabric available from W. L. GORE & ASSO- CIATES® of Newark, Del., United States, although other membranes will fall within the scope of the present disclosure as well.

Each of the cathode plate 304 and the anode plate 306 may include a carbon backed metalized substrate with a titanium mesh substrate plated on the carbon membrane, which provides a complete coverage area for electrical conductance to the PEM 302. Electrical contact to the power subsystems 112/206 and the transfer of power from the power subsystems 112/206 to the cathode and anode plates 304 and 306 may be provided by, for example, attaching a copper strip to the titanium mesh substrate on the cathode plate 304 and anode plate 306 (e.g., using epoxy), with the compressive force applied by the flange bolting subsystem 308 operating to provide the necessary adhesion to the surfaces of the cathode plate 304 and anode plate 306. A valve 310 is coupled to an oxygen outlet 306a defined by the anode plate 306 and may include fittings, connectors, and/or other couplings that are configured to couple to the oxygen flow coupling that extends to the oxygen outlets 120/212. For example, the valve 310 may be provided by a 304L stainless steel needle discharge valve utilizing viton seats, and machined for connection to the anode plate 306 using a viton O-ring (not illustrated.) While a specific oxygen production subsystem 300 has been described, one of skill in the art in possession of the present disclosure will recognize that other oxygen production subsystems may be provided in the wound oxygen supply systems described herein while remaining within the scope of the present disclosure.

Figure 4A:
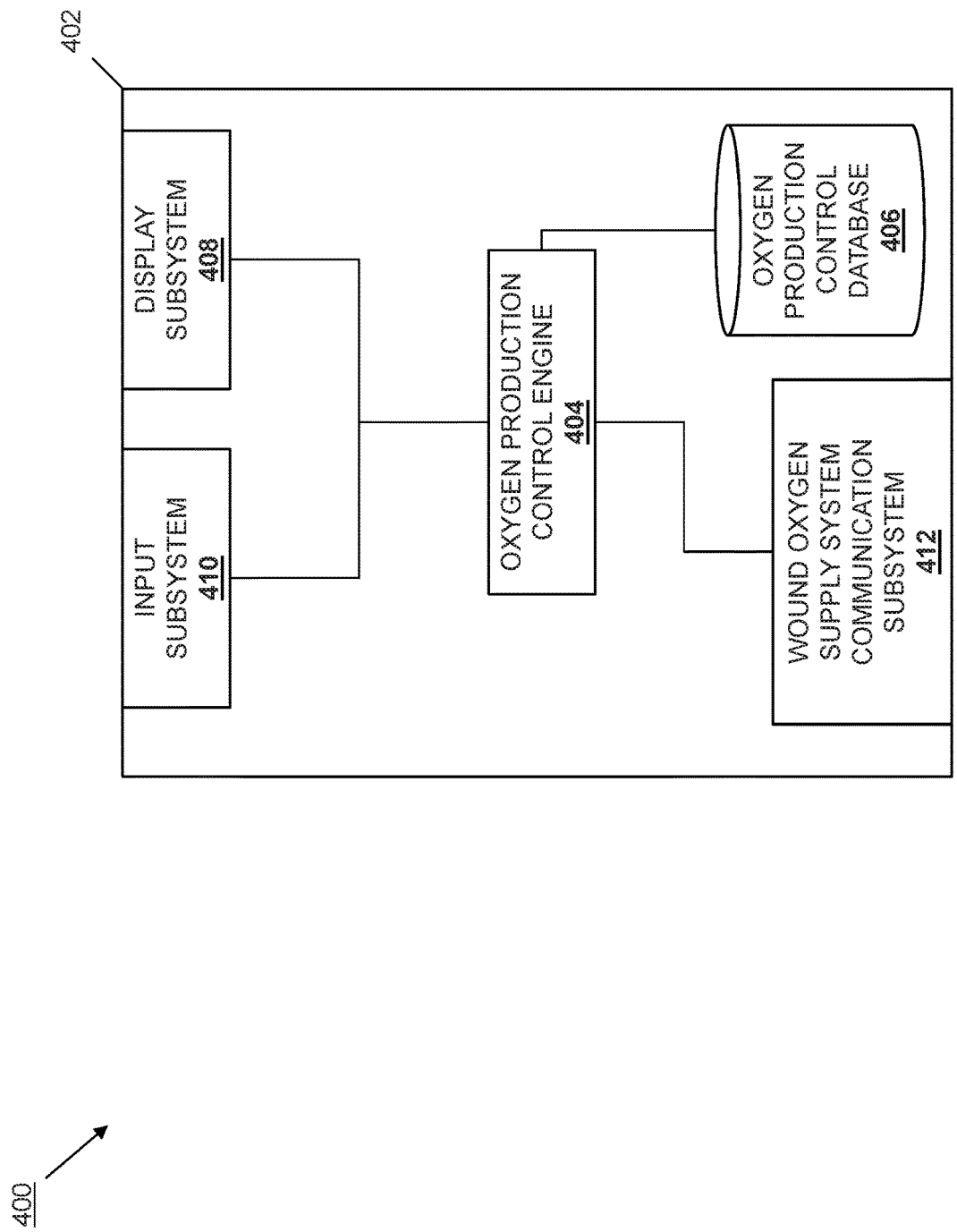
FIG. 4A is a schematic view illustrating an embodiment of a control device that may be used to control the wound oxygen supply system of FIGS. 2A-2C.
Figure 4B:
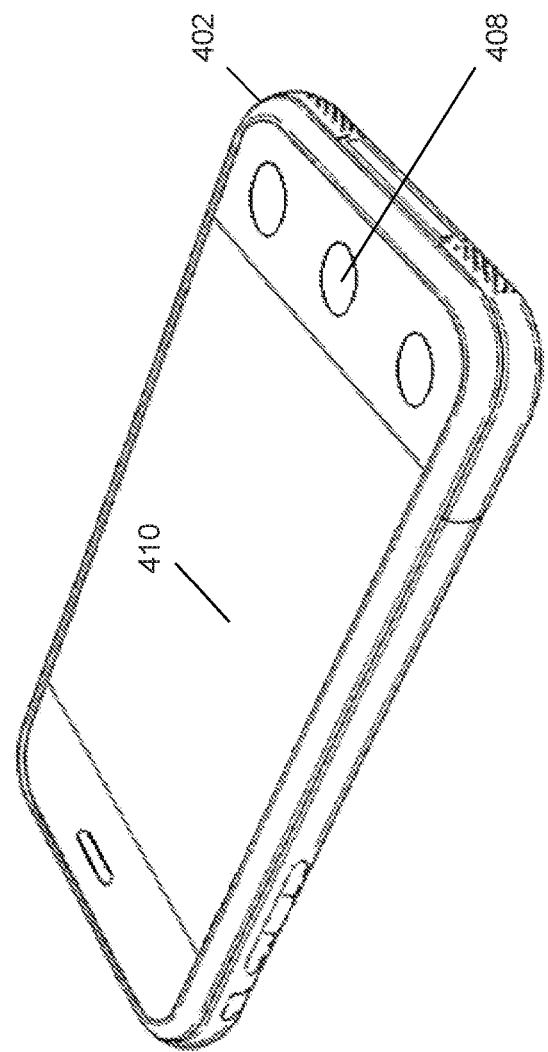
FIG. 4B is a perspective view illustrating an embodiment of the control device of FIG. 4A.

Referring now to FIGS. 4A and 4B, an embodiment of a control device 400 is illustrated. In the embodiments illustrated and discussed below, the control device 400 is provided by a mobile phone. However, other computing devices such as, for example, tablet computing devices, laptop/notebook computing devices, desktop computing devices, smart watches, fitness trackers or other wrist mounted devices, and/or a variety of other computing devices may be provided as the control device 400 while remaining within the scope of the present disclosure. The control device 400 includes a chassis 402 that houses the components of the control device, only some of which are illustrated in FIG. 4A. For example, the chassis 402 may house a processing subsystem (not illustrated, but which may include one or more hardware processors known in the art) and a memory subsystem (not illustrated, but which may include one or more memory devices known in the art) that includes instructions that, when executed by the processing subsystem, cause the processing subsystem to provide an oxygen production control engine 404 that is configured to perform the functions of the oxygen production control engines and control devices discussed below. The chassis 402 may also house a storage subsystem (not illustrated, but which may include one or more storage devices known in the art) that is coupled to the oxygen production control engine 404 (e.g., via a coupling between the storage subsystem and the processing subsystem), and that stores an oxygen production control database 406 that may include any of the information utilized to provide the functionality discussed below.

The chassis 402 may also house and/or include a display subsystem 408 that is coupled to the oxygen production control engine 404 (e.g., via a coupling between the display subsystem 408 and the processing subsystem) and that is configured to display any of the information discussed below. The chassis 402 may also house an input subsystem 410 that is coupled to the oxygen production control engine 404 (e.g., via a coupling between the input subsystem 410 and the processing subsystem) and that is configured to receive and provide any of the input information to the oxygen production control engine 404 as discussed below. While the display subsystem 408 and the input subsystem 410 are illustrated and described as separate subsystems, one of skill in the art in possession of the present disclosure will recognized that they may be combined (e.g., in a touch-input display subsystem) while remaining within the scope of the present disclosure. The chassis 402 may also house a wound oxygen supply system communication subsystem 412 that may include wired and/or wireless communication components (e.g., BLUETOOTH® subsystems, Near Field Communication (NFC) subsystems, WiFi communication subsystems, wired connector subsystems, etc.) that provide for the wound oxygen supply device communication functionality discussed below. As such, the wound oxygen supply system communication subsystem 412 may provide for the control described below via a variety of wireless or wired connections (e.g., local wired or wireless connections, wired or wireless Internet connections, etc.) While a specific control device 400 has been illustrated and described, one of skill in the art in possession of the present disclosure will recognize that control devices utilized in the present disclosure may include a variety of other components (e.g., mobile phone components) that provide a variety of conventional functionality in addition to the functionality discussed below while remaining within the scope of the present disclosure.

Figure 5:
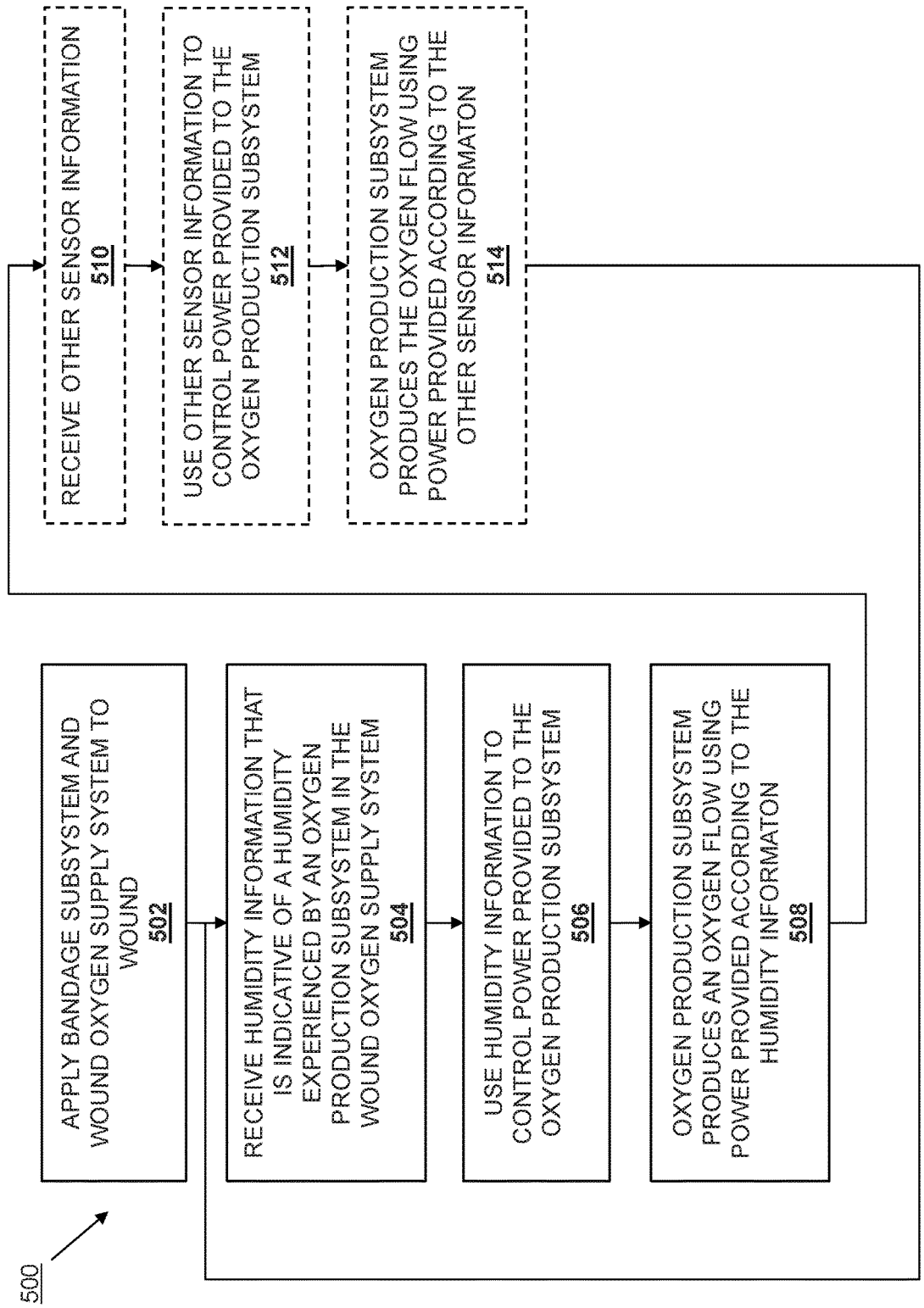
FIG. 5 is a flow chart illustrating an embodiment of a method for supplying oxygen to a wound.

Referring now to FIG. 5, an embodiment of a method 500 for supplying oxygen to a wound is illustrated. As discussed above, the inventors of the present disclosure invented the systems and methods described in U.S. Pat. No. 8,287,506, and child patents thereof such as U.S. Patent Publication No. 2016/0082238, which discuss and claim wound treatment systems that provides for low dose tissue oxygenation and continuous oxygen adjustability to wound site(s), and operate by monitoring pressure information that is indicative of a pressure in a restricted airflow enclosure that is located adjacent a wound site (e.g., provided by a wound dressing), and using the pressure information to control power provided to an oxygen production subsystem in order to control an oxygen flow that is created by the oxygen production subsystem and provided to the restricted airflow enclosure. Those wound treatment systems may include a flow sensor that measures the oxygen flow generated by an oxygen output of the oxygen production subsystem, and a pressure sensor downstream of the flow sensor, the outputs of which may be utilized to control the oxygen flow created by the oxygen production subsystem as discussed above. However, as also discussed above, the flow sensor utilized with such wound treatment systems is relatively large, relatively expensive, and requires "plumbing" that takes up space in the wound treatment system chassis and results in a relatively large chassis. Furthermore, it has also been discovered that oxygen production subsystems utilized with such wound treatment systems may provide reduced oxygen production as humidity decreases, which can result in deficient wound site oxygen supply, and can cause the wound treatment systems to increase the power provided to the oxygen production subsystem to a level that can damage the oxygen production subsystem.

The systems and methods of the present disclosure address these issues by providing a humidity sensor subsystem in the wound oxygen supply system, and utilizing the humidity sensor subsystem to monitor the humidity experienced by the oxygen production subsystem, and report humidity information to an oxygen production control engine that is indicative of that humidity. The oxygen production control engine then uses the humidity information to control the power provided by a power subsystem to the oxygen production subsystem in order to control an oxygen flow that is created by the oxygen production subsystem and provided through an oxygen outlet to a restricted airflow enclosure adjacent a wound. In some examples, oxygen production control data may be generated that associates, for each of a plurality of different power amounts, a varying oxygen output of the oxygen production system over a range of changing humidity levels, and that oxygen production control data may be stored in an oxygen production control database. As such, the oxygen production control engine may have access to data that indicates, for any particular humidity level, a power that may be applied to the oxygen production subsystem to produce a desired oxygen output and associated oxygen flow rate. Thus, using the humidity information received from the humidity sensor subsystem, the oxygen production control engine may cause the power subsystem to provide an amount of power to the oxygen production subsystem that causes the creation of oxygen and a subsequent desired oxygen output/flow to the restricted airflow enclosure adjacent the wound.

The systems and methods of the present disclosure allow for the conventional flow sensor subsystems utilized in the wound treatment systems discussed above to be replaced with the humidity sensor subsystem described herein, providing a reduction in the cost and space required for the sensor subsystem that is utilized to control the production of oxygen by the oxygen production subsystem. For example, as discussed above, conventional flow sensor subsystems cost approximately $60 USD, measure approximately 36 mm by 20 mm, consumes a relatively high amount of energy (up to 40 milliamps (ma)), and requires "plumbing" that includes tubing that connects the flow sensor to the oxygen flow(s) that it measures and that dictates particular positioning of the flow sensor in the chassis to allow the routing of such tubing. To contrast, the humidity sensor subsystem of the present disclosure costs approximately $1.50. USD, measure approximately 3 mm by 3 mm, consumes minimal energy (less than 1 milliamp (ma)), and utilizes a relatively simple coupling system that may be mounted anywhere on a circuit board (e.g., that includes the processing system that provides the oxygen production control engine.) As such, reductions in the size of the wound treatment system chassis are provided while still enabling low dose tissue oxygenation and continuous oxygen adjustability to wound site. Furthermore, the control of oxygen production based on the humidity experienced by the oxygen production subsystem prevents deficient wound site oxygen supply that conventional wound treatment systems experience in low humidity environments, and prevents problems associated with increases in power that are provided to the oxygen production subsystem to address the reduced oxygen production capabilities that result from such low humidity environments.

Figure 6:
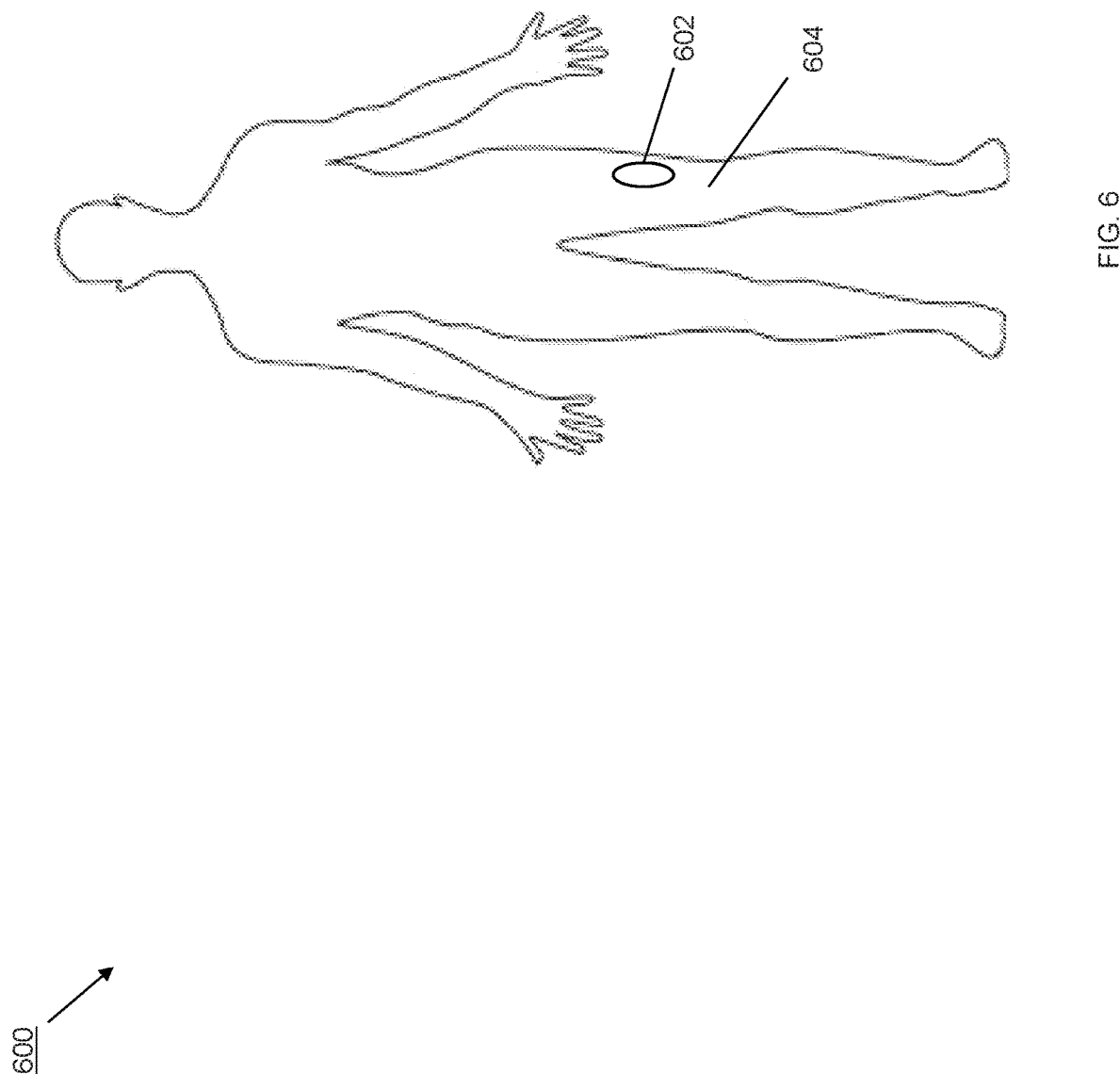
FIG. 6 is a schematic view illustrating an embodiment of a patient with a wound.

The method 500 begins at block 502 where a bandage subsystem and a wound oxygen supply system are applied to a wound. Referring now to FIG. 6, at or before block 502, a patient 600 may be provided including at least one wound. In many of the specific embodiments discussed below, the at least one wound is a single wound 602 that is located on a surface of a leg 604 of the patient 600, and that may extend at least partially into the leg 604 of the patient 600. However, as discussed below, in some embodiments, a patient may include more than one wound, and the wounds may be located on any portion of the body of the patient 600. Furthermore, in some embodiments, wounds may be located within the patient 602 (e.g., beneath unwounded, repaired (e.g., surgically repaired), or otherwise healthy skin of the patient), such as on an organ of the patient 600, and thus the wound oxygen supply systems of the present disclosure may be provided internally to the patient 600 while remaining within the scope of the present disclosure. In such internal wound oxygen supply systems, the functionality discussed below may be supplemented by the removal of oxygen that provided to the wound (e.g., via oxygen removal tubing similar to the oxygen provisioning tubing discussed below.) Wounds subject to treatment using the wound oxygen supply systems and methods of the present disclosure may include ulcers (diabetic, venous, arterial, pressure, etc.), surgical incisions or closures, amputations, burns, frostbite, insect or animal bites, organ or tissue transplants, organ or tissue implants, tissue grafting, and/or any other wound that would be apparent to one of skill in the art in possession of the present disclosure.

Figure 7A:
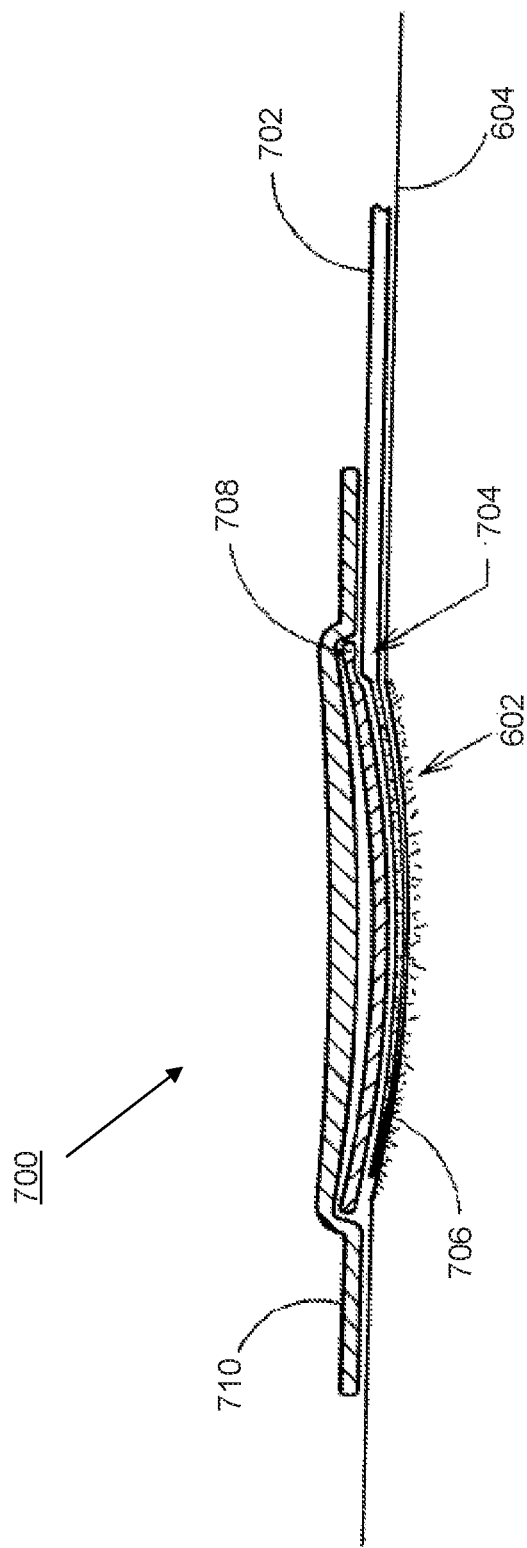
FIG. 7A is a cross sectional view illustrating an embodiment of a bandage subsystem positioned on the wound of the patient of FIG. 5.

Referring to FIG. 7A, in an embodiment, at block 502 a bandage subsystem 700 may be positioned adjacent the wound 602 on the leg 604 of the patient 600. In the illustrated embodiment, the bandage subsystem 700 includes tubing 702 that, as discussed above, may be connected on a first end (not illustrated) to the oxygen outlet 120 on the wound oxygen supply system 100, and that includes a second end 704 that is located opposite the tubing 702 from the first end. An oxygen permeable membrane 706 extends from the second end 704 of the tubing 702, and may be integrated with the tubing 702, coupled to the tubing 702, and/or provided in a variety of manners that would be apparent to one of skill in the art in possession of the present disclosure. For example, the oxygen permeable membrane 706 may be provided by oxygen distribution tape that is positioned over the second end 704 of the tubing and the wound 602 (e.g., such that it engages the intact skin adjacent the wound 602.) However, the oxygen permeable membrane 706 may be provided using a variety of materials that would be apparent to one of skill in the art in possession of the present disclosure. As can be seen in the illustrated embodiment, the oxygen permeable membrane 706 may be positioned on, around, or otherwise adjacent the wound 602 on the leg 604 of the patient 600, and may be covered with a moisture absorbent dressing 708 (covering the oxygen permeable membrane 706 and any of the exposed wound 602, if present) that is further covered by a reduced vapor pressure, permeable, occlusive dressing 710 (e.g., that covers the moisture absorbent dressing 708, the oxygen permeable membrane 706, the wound 602, and a portion of the tubing 702), creating a restricted airflow enclosure adjacent the wound 602 (e.g., between the wound and the dressing 710.) In an embodiment, the dressing 710 may be made of a transparent material, and is configured to trap oxygen introduced into the restricted airflow enclosure adjacent the wound 602 to create and maintain an oxygen rich environment. Experimental embodiments have found that the local partial pressure of oxygen at the wound 602 may be increased from a low range of 10 to 60 mm Hg to an oxygen rich environment range of 200 to 760 mm HG using the bandage subsystem and wound oxygen supply system of the present disclosure. In some embodiments, the bandage subsystem 700 may incorporate a pressure release valve that is configured to ensure that the pressure in the restricted airflow enclosure provided by the dressing 710 does not exceed a maximum desired level.

Figure 7B:
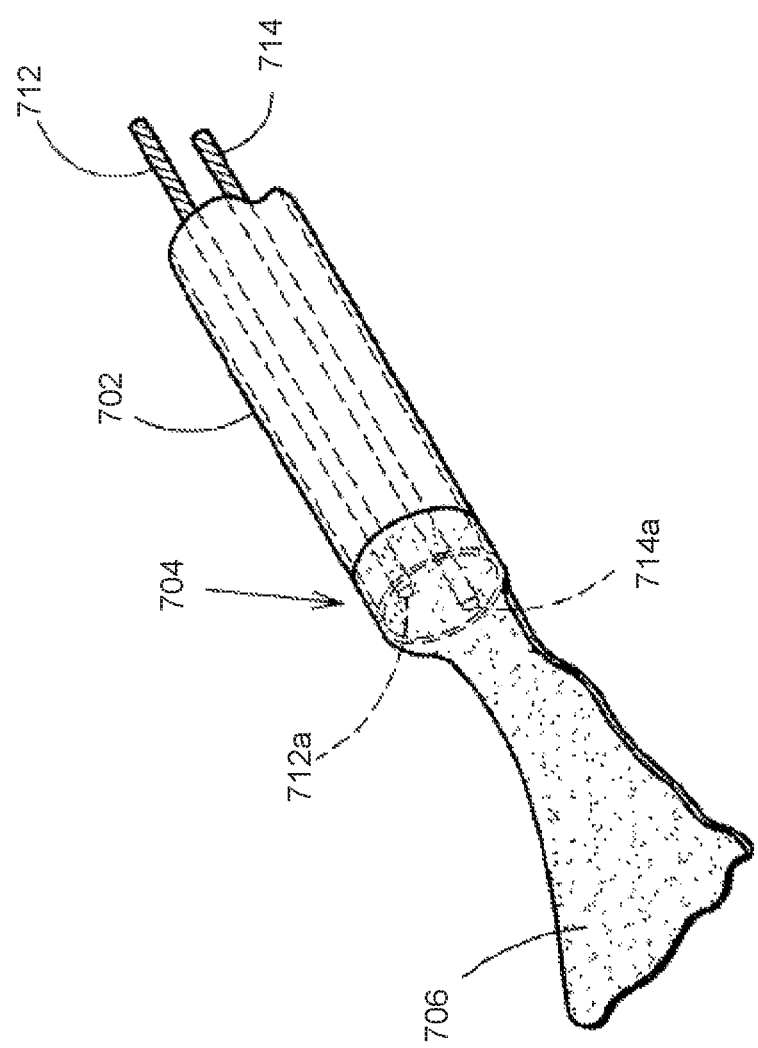
FIG. 7B is a perspective view illustrating an embodiment of tubing and an oxygen permeable membrane that is may be included in the bandage subsystem of FIG. 7A.

In some embodiments, the bandage subsystem 700 may provide sensors that may be located in the tubing 702 and/or in the oxygen permeable membrane 706 (i.e., such that they may be positioned in the restricted airflow enclosure provided by the bandage subsystem 700.) For example, FIG. 7B illustrates how sensor couplings 712 and 714 may extend through the tubing 702 and may include sensors 712a and 712b located on their distal ends and positioned in the tubing 702 and/or the oxygen permeable membrane 706. For example, the sensor couplings 712/714 and sensors 712a/714a may be part of or provided by the humidity sensor subsystems 122a/214a, the pressure sensor subsystems 122b/214b, and/or the other sensor subsystems 122c/214c (e.g., the flow sensor subsystems, the temperature sensor subsystems, and/or any of the other sensor subsystems described herein, as well as sensors that may provide for other monitoring of the wound 602.) In a specific example, the sensor couplings 712/714 may be provided by sensor wires that extend through the tubing 702 between the sensors 712a/714a and sensor transducers in the chassis 102 that provide input to the oxygen production control engine. However, while a specific embodiment of sensor subsystems located outside of the chassis 102 of the wound oxygen supply system 100 has been described, sensor subsystems may be located within and outside of the chassis 102 of the wound oxygen supply system 100 in a variety of manners that will fall within the scope of the present disclosure as well.

Figure 7C:
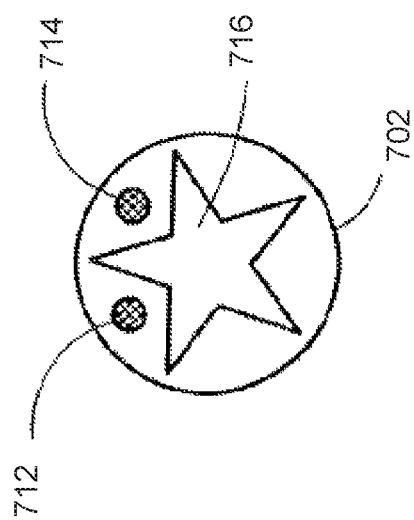
FIG. 7C is a cross sectional view illustrating an embodiment of the tubing of FIG. 7B.
Figure 7D:
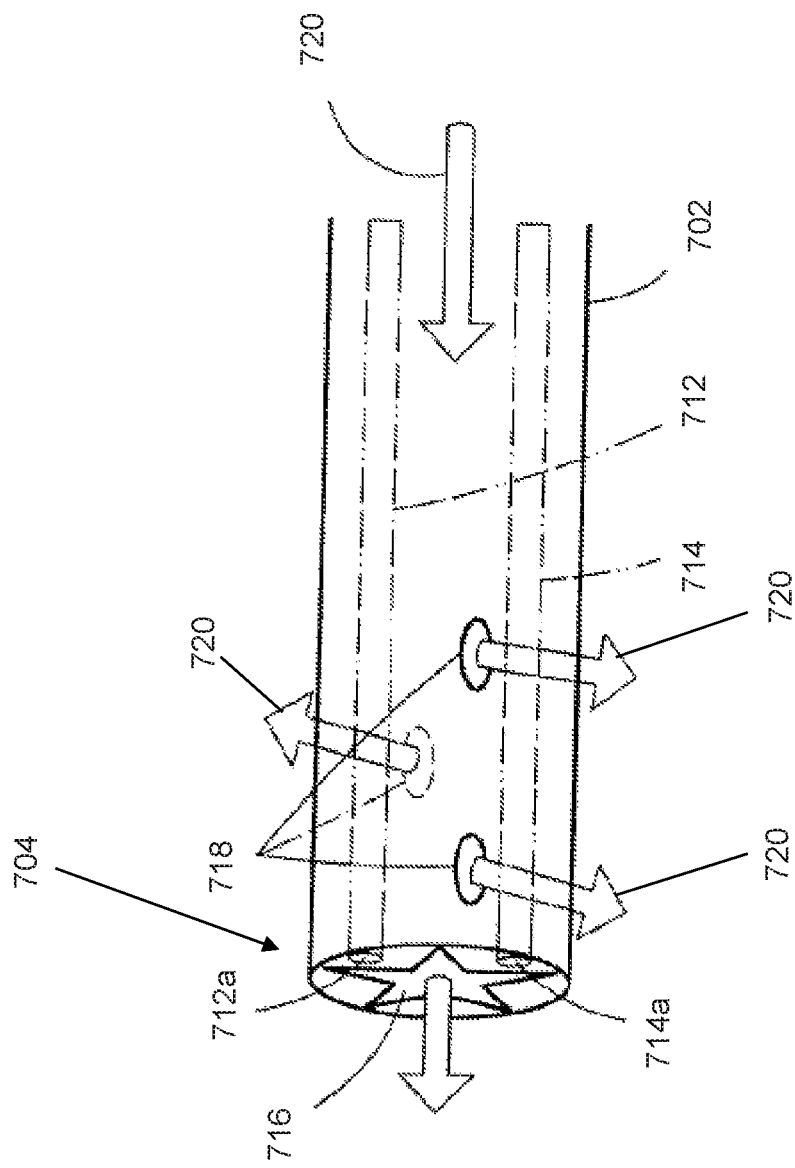
FIG. 7D is a perspective view illustrating an embodiment of the tubing of FIG. 7C.

Referring now to FIG. 7C, the tubing 702 may include a plurality of lumens, including an inner lumen 716 that, in the illustrated embodiment, is provided with a star-like configuration that operates to resist kinking of the tubing 702 while still providing for oxygen flow if the tubing 702 is bent. However, a variety of other kink-resistant components and/or materials may be provided with the tubing 702 to provide similar functionality while remaining within the scope of the present disclosure. FIG. 7D illustrates how the tubing 702 may define a plurality of apertures 718 adjacent the second end 704 of the tubing 702 to aid in the delivery of oxygen to the wound 602. As such, an oxygen flow 720 produced by the oxygen production subsystem and directed through the tubing 702 to the wound 602 may exit the tubing 702 and enter the restricted airflow enclosure adjacent the wound 702 through the multiple different apertures 718, as well as through a distal end of inner lumen 716, improving the flow of oxygen to the wound 602.

Figure 8:
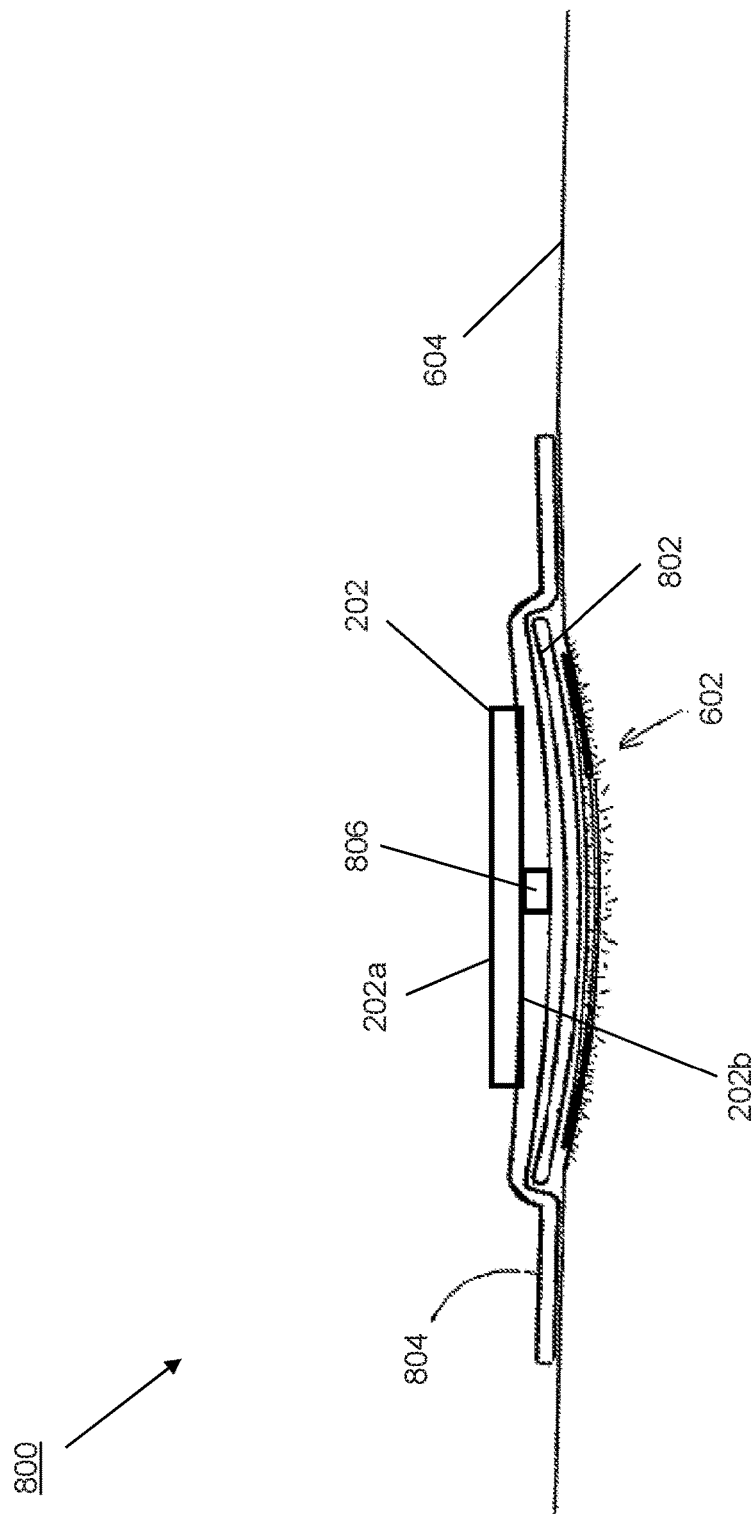
FIG. 8 is a cross sectional view illustrating an embodiment of the wound oxygen supply system of FIGS. 2A-2C included as part of a bandage subsystem that is positioned on the wound of the patient of FIG. 6.

Referring to FIG. 8, in an embodiment, at block 502 a bandage subsystem/wound oxygen supply system 800, which includes the wound oxygen supply system 200 of FIGS. 2A-2C coupled to or integrated into a bandage system, may be positioned adjacent the wound 602 on the leg 604 of the patient 600. In the illustrated embodiment, the bandage subsystem 800 includes a moisture absorbent dressing 802 covering the wound 602, and a reduced vapor pressure, permeable, occlusive dressing 804 (e.g., that covers the moisture absorbent dressing 802 and the wound 602), creating a restricted airflow enclosure adjacent the wound 602 (e.g., between the wound and the dressing 804.) In an embodiment, the dressing 804 may be made of a transparent material, and is configured to trap oxygen introduced into the restricted airflow enclosure adjacent the wound 602 to create and maintain an oxygen rich environment. In the illustrated embodiment, the wound oxygen supply system 200 is coupled to or integrated into the dressing 804, which includes an oxygen channel 806 that is configured to channel oxygen generated by the wound oxygen supply system 200 and provided via the oxygen outlet 212 into the restricted airflow enclosure created by the dressing 804 and located adjacent the wound 602. Experimental embodiments have found that the local partial pressure of oxygen at the wound 602 may be increased from a low range of 10 to 60 mm Hg to an oxygen rich environment range of 200 to 760 mm HG using the bandage subsystem/wound oxygen supply system of the present disclosure.

While not illustrated in the embodiment of FIG. 8, in some embodiments, the bandage subsystem/wound oxygen supply system 800 may include an oxygen permeable membrane that is similar to the oxygen permeable membrane 706 discussed above. For example, an oxygen permeable membrane may be coupled to the oxygen outlet 212 on the wound oxygen supply system 200 (e.g., via the oxygen channel 806) and located immediate adjacent the wound 602 (e.g., via the oxygen channel 806 that may, for example, extend through the moisture absorbent dressing 802.) However, one of skill in the art in possession of the present disclosure will recognize that an oxygen permeable membrane may be provided in the bandage subsystem/wound oxygen supply system 800 in a variety of manners that will fall within the scope of the present disclosure as well. While also not illustrated in the embodiment of FIG. 8, the bandage subsystem/wound oxygen supply system 800 may include sensors that are located outside of the chassis 202 of the wound oxygen supply system 200 (i.e., such that they are positioned in the oxygen channel 806, an oxygen permeable membrane included in the bandage subsystem/wound oxygen supply system 800, and/or the restricted airflow enclosure provided by the bandage subsystem/wound oxygen supply system 800) in substantially the same manner as described above with the wound oxygen supply system 100.

While a few specific examples of bandage subsystems coupled to and integrated with the wound oxygen supply systems 100 and 200 have been illustrated and described, a variety of modifications and combinations of those examples are envisioned as falling within the scope of the present disclosure. For example, the wound oxygen supply system 200 may be coupled to tubing that is similar to the tubing 702 discussed above and that provides oxygen created by the wound oxygen supply system 200 to a bandage subsystem that is similar to the bandage subsystem 700 discussed above. Similarly, the wound oxygen supply system 200 may be coupled to or integrated into a bandage subsystem that is similar to the bandage subsystem/wound oxygen supply system 800 discussed above. Furthermore, one of skill in the art in possession of the present disclosure will recognize how the bandage subsystems may be modified to provide a bandage subsystem (with a tubing-coupled wound oxygen supply system, an integrated wound oxygen supply system, etc.) that is configured to be provided on a wound that is internal to the patient 600 (e.g., beneath the skin of the patient such as, for example, located on an internal organ of the patient 600) so that oxygen may be provided to internal wounds using the teachings of the present disclosure. As such, one of skill in the art in possession of the present disclosure will recognize that a wide variety of modifications to the teachings of the present disclosure will thus fall within its scope.

Figure 9:
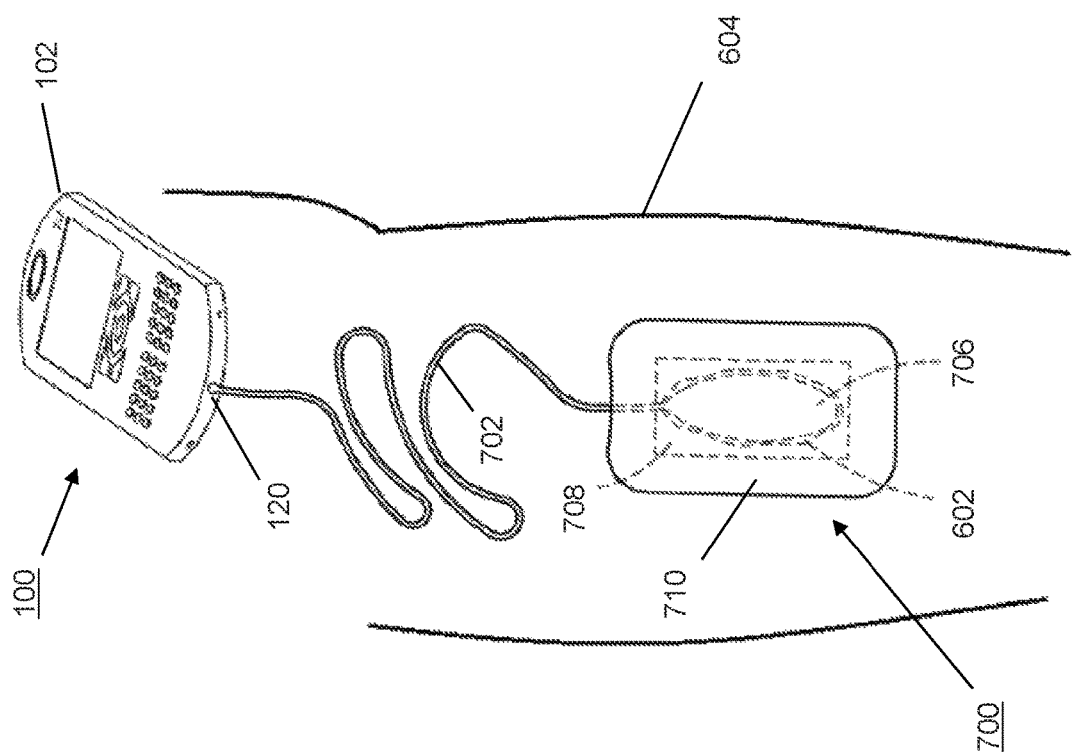
FIG. 9 is a front/perspective view illustrating an embodiment of the wound oxygen supply system of FIGS. 1A-1B coupled to the bandage subsystem of FIG. 7A that is positioned on the wound of the patient of FIG. 6.

The method 500 then proceeds to block 504 where humidity information is received that is indicative of a humidity experienced by the oxygen production subsystem in the wound oxygen supply system. Referring to FIGS. 7A and 9, the bandage subsystem 700 is illustrated coupled to the patient 600 and providing a restricted airflow enclosure adjacent the wound 602, with the tubing 702 extending from the bandage subsystem 700 to the oxygen outlet 120 on the wound oxygen supply system 100. One of skill in the art in possession of the present disclosure will recognize that the configuration of the bandage subsystem 700 and the wound oxygen supply system 100 allows the wound oxygen supply system 100 to be comfortably positioned at a variety of locations on and/or adjacent the patient (e.g., on a belt, in a pocket, in a bag, strapped to a limb, etc.) In an embodiment, at block 504, the humidity sensor subsystem 122a in the wound oxygen supply system 100 may operate to detect a humidity level (e.g., within the chassis 102 of the wound oxygen supply system 100, adjacent to and outside the chassis 102 of the wound oxygen supply system 100, in the tubing 702, in the restricted airflow enclosure provided by the bandage subsystem 700, etc.) and, in response, generate humidity information that is indicative of that humidity level that is being experienced by the oxygen production subsystem 116 (and that effects the oxygen production operations of that oxygen production subsystem 116 as discussed above.) The humidity sensor subsystem 122a and/or the oxygen production control engine 104 may then operate such that, at block 504, the oxygen production control engine 104 receives the humidity information generated by the humidity sensor subsystem 122a.

Figure 10:
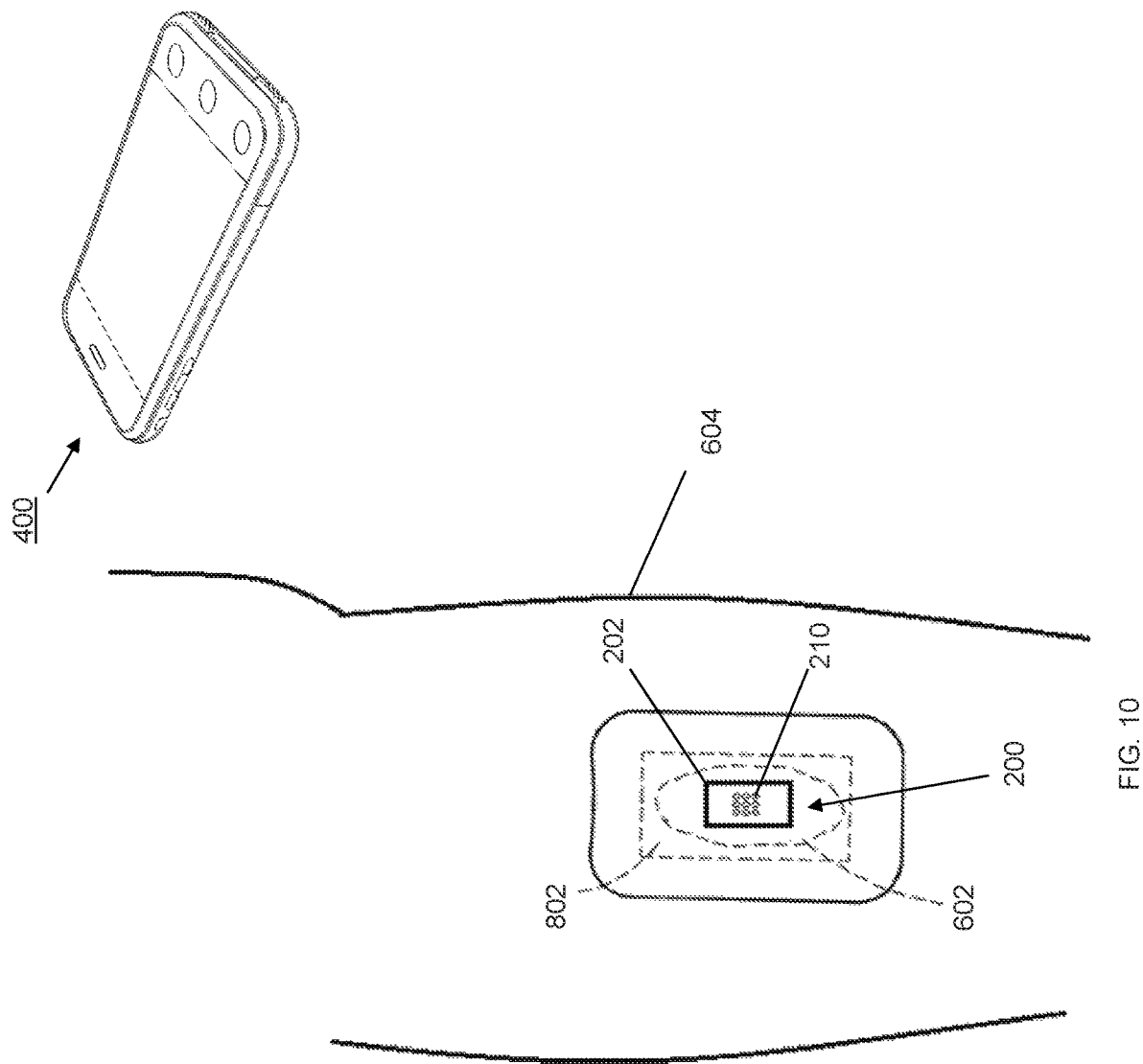
FIG. 10 is a front/perspective view illustrating an embodiment of the control device of FIGS. 4A-4B controlling the wound oxygen supply system and bandage subsystem of FIG. 9A.

Referring to FIGS. 8 and 10, the bandage subsystem/wound oxygen supply system 800 is illustrated coupled to the patient 600 and providing a restricted airflow enclosure adjacent the wound 602, with the control device 400 communicatively coupled to the wound oxygen supply system 200. For example, prior to or at block 504, the wound oxygen supply system communication subsystem 412 in the control device 400 and the control device communication subsystem 204 in the wound oxygen supply system 200 may enable the wound oxygen supply system 200 and the control device to pair (e.g., via a BLUETOOTH® or other wireless communication pairing protocol), link, and/or otherwise establish a communication channel such that they may exchange data or other information as discussed below. One of skill in the art in possession of the present disclosure will recognize that the configuration of the bandage subsystem/wound oxygen supply system 800 and the control device 400 allows the bandage subsystem/wound oxygen supply system 800 to be provided on a wound, and the control device 400 to be comfortably positioned at a variety of locations on and/or adjacent the patient (e.g., on a belt, in a pocket, in a bag, strapped to a limb, etc.) while still enabling control of the wound oxygen supply system 200.

In an embodiment, at block 504, the humidity sensor subsystem 214b in the wound oxygen supply system 200 may operate to detect a humidity level (e.g., within the chassis 202 of the wound oxygen supply system 200, adjacent to and outside the chassis 202 of the wound oxygen supply system 200, in the oxygen channel 806, in the restricted airflow enclosure provided by the bandage subsystem/wound oxygen supply system 800, etc.) and, in response, generate humidity information that is indicative of that humidity level that is being experienced by the oxygen production subsystem 208 (and that effects the oxygen production operations of that oxygen production subsystem 208 as discussed above.) The humidity sensor subsystem 122a and/or the control device communication subsystem 204 may then operate such that the control device communication subsystem 204 receives the humidity information generated by the humidity sensor subsystem 122a. The control device communication subsystem 204 may then operate at block 504 to transmit, via the communication connection with the control device 400 established as discussed above, the humidity information to the control device 400 such that the oxygen production control engine 404 receives that humidity information through the wound oxygen supply system communication subsystem 412.

The method 500 then proceeds to block 506 where the humidity information is used to control the power provided to the oxygen production subsystem. In an embodiment, with reference to the bandage subsystem 700 and wound oxygen supply system 100 discussed above, at block 506 the oxygen production control engine 104 uses the humidity information received from the humidity sensor subsystem 122a to control the power provided by the power subsystem 112 to the oxygen production subsystem 116. For example, as discussed above, the oxygen production control database 106 may include oxygen production control data that associates, for each of a plurality of different power amounts, a varying oxygen output of the oxygen production subsystem 116 over a range of different humidity levels. As such, at block 506, the oxygen production control engine 104 may determine a desired oxygen flow rate or pressure in the restricted airflow enclosure (e.g., as programmed in the wound oxygen supply system 100), and access the oxygen production control data and determine, using the particular humidity level indicated by the humidity information received at block 504, a particular power amount that will cause the oxygen production subsystem 116 to produce an oxygen output that will provide that desired oxygen flow rate or pressure in the restricted airflow enclosure. The oxygen production control engine 104 may then cause the power subsystem 112 to provide that particular power amount to the oxygen production subsystem 116 by, for example, sending an instruction to the power subsystem 112 to transmit that power amount to the oxygen production subsystem 116. However, while the use of previously generated oxygen production control data has been described, one of skill in the art in possession of the present disclosure will recognize that other methods for controlling the power provided by the power subsystem 112 to the oxygen production subsystem 116 using the humidity information (e.g., via an equation that computes a power amount in response to a provided humidity level, etc.) will fall within the scope of the present disclosure as well.

In another embodiment, with reference to the bandage subsystem/wound oxygen supply system 800 and the control device 400 discussed above, at block 506 the oxygen production control engine 404 uses the humidity information received from the humidity sensor subsystem 214a to control the power provided by the power subsystem 206 to the oxygen production subsystem 208. For example, similarly as discussed above, the oxygen production control database 406 may include oxygen production control data that associates, for each of a plurality of different power amounts, a varying oxygen output of the oxygen production subsystem 208 over a range of different humidity levels. As such, at block 506, the oxygen production control engine 404 may determine a desired oxygen flow rate or pressure in the restricted airflow enclosure (e.g., as programmed in the wound oxygen supply system 100), and access the oxygen production control data and determine, using the particular humidity level indicated by the humidity information received at block 504, a particular power amount that will cause the oxygen production subsystem 208 to produce an oxygen output that will provide that desired oxygen flow rate or pressure in the restricted airflow enclosure. The oxygen production control engine 404 may then transmit an instruction via the wound oxygen supply system communication subsystem 412 to the control device communication subsystem 204 in the wound oxygen supply system 200, and the control device communication subsystem 204 may, in response, cause the power subsystem 206 to provide that particular power amount to the oxygen production subsystem 208 by, for example, forwarding that instruction to the power subsystem 206 to transmit that power amount to the oxygen production subsystem 208. However, while the use of previously generated oxygen production control data has been described, one of skill in the art in possession of the present disclosure will recognize that other methods for controlling the power provided by the power subsystem 206 to the oxygen production subsystem 208 using the humidity information (e.g., via an equation that computes a power amount in response to a provided humidity level, etc.) will fall within the scope of the present disclosure as well.

The method 500 then proceeds to block 508 where the oxygen production subsystem produces an oxygen flow using the power provided according to the humidity information. In an embodiment, with reference to either the bandage subsystem 700 and wound oxygen supply system 100 or the bandage subsystem/wound oxygen supply system 800 discussed above, at block 508 the oxygen production subsystem 116/208 uses the power provided by the power subsystem 112/206 at block 506 to generate oxygen and product an oxygen flow. For example, upon receiving the power amount from the power subsystem 112/206, the oxygen production subsystem 116/208 will operate to draw air in through the oxygen inlet 118/210 that includes approximately 21% oxygen, and that air is then directed through the oxygen production subsystem 116/208, which operates to perform an electrochemical process that concentrates the oxygen included in that air to create an oxygen mixture that approximately 99% pure oxygen, and provides that oxygen mixture as an oxygen flow that is directed to the oxygen outlet 120/212. The power amount (e.g., the current) provided by the power subsystem 112/206 may operate to provide for proportional or otherwise related oxygen generation (i.e., oxygen concentration from the air received through the oxygen inlet 118/210), thereby producing the oxygen flow with an oxygen flow rate that is proportion or otherwise related to the amount of power supplied by the power subsystem 112/206 to the oxygen production subsystem 116/208 (e.g., increasing the current increases the electrochemical process performed by the oxygen production subsystem 116/208 and thereby increases the subsequent oxygen flow rate produced by the oxygen production subsystem 116/208, while decreasing the current decreases the electrochemical process performed by the oxygen production subsystem 116/208 and thereby decreases the subsequent oxygen flow rate produced by the oxygen production subsystem 116.) In a specific example, the power subsystem 112/206 may include lithium batteries (e.g., 7.4 volt lithium batteries) and a regulator that is configured to vary the amperage over a range of approximately 15 milliamps to approximately 150 milliamps, which operates to provide oxygen flow rates in the range of approximately 1.0 milliliters/hour to approximately 15.0 milliliters/hour. However, a variety of other power subsystem configurations may be utilized to provide a variety of different power amounts and subsystem oxygen flow rates while remaining within the scope of the present disclosure.

The oxygen flow generated by the oxygen production subsystem 116/208 is then directed out of the chassis 102/202 via the oxygen outlet 120/212. In an embodiment, with reference to the bandage subsystem 700 and wound oxygen supply system 100 discussed above, the oxygen flow generated by the oxygen production subsystem 116 may exit the oxygen outlet 120 and enter the tubing 702, and be directed by the tubing 702 to the oxygen permeable membrane 706 such that the oxygen flow is introduced into the restricted airflow enclosure provided by the bandage subsystem 700.

In another embodiment, with reference to the bandage subsystem/wound oxygen supply system 800 discussed above, the oxygen flow generated by the oxygen production subsystem 208 may exit the oxygen outlet 202 and be directed by the oxygen channel 806 such that the oxygen flow is introduced into the restricted airflow enclosure provided by the bandage subsystem 700. In either embodiment, the increased available oxygen provided in the oxygen flow introduced to the restricted airflow enclosure may be metabolized at the cellular level, and will operate to stimulate an increase in growth factors, epithelialization, granulation tissue, glycosaminoglycan production, and collagen synthesis.

The method 500 then proceeds to optional block 510 where other sensor information may be received. In some embodiments, other sensor information may be generated by the wound oxygen supply system and utilized in a variety of manners, a few of which are discussed below. However, in embodiments where system size and cost are to be minimized, the humidity sensor subsystem and use of humidity information to control the oxygen flow created by the oxygen production subsystem have been found to be sufficient in providing for enhanced wound healing as discussed above. In an embodiment, with reference to the bandage subsystem 700 and wound oxygen supply system 100 discussed above, at block 510 any other sensor subsystem(s) provided in the wound oxygen supply system 100 may operate to sense, measure, and/or otherwise detect a variety of factors (e.g., within the chassis 102 of the wound oxygen supply system 100, adjacent to and outside the chassis 102 of the wound oxygen supply system 100, in the tubing 702, in the restricted airflow enclosure provided by the bandage subsystem 700, etc.) and, in response, generate information that is indicative of that factor. Those other sensor subsystem(s) and/or the oxygen production control engine 104 may then operate such that, at block 504, the oxygen production control engine 104 receives the other sensor information generated by those other sensor subsystem(s).

In another embodiment, with reference to the bandage subsystem/wound oxygen supply system 800 discussed above, at block 510 any other sensor subsystem(s) provided in the wound oxygen supply system 200 may operate to sense, measure, and/or otherwise detect a variety of factors (e.g., within the chassis 202 of the wound oxygen supply system 200, adjacent to and outside the chassis 202 of the wound oxygen supply system 200, in the oxygen channel 806, in the restricted airflow enclosure provided by the bandage subsystem/wound oxygen supply system 800, etc.) and, in response, generate information that is indicative of that factor. Those other sensor subsystem(s) and/or the control device communication subsystem 204 may then operate such that the control device communication subsystem 204 receives the other sensor information generated by those other sensor subsystem(s). The control device communication subsystem 204 may then operate at block 504 to transmit, via the communication connection with the control device 400 established as discussed above, the other sensor information to the control device 400 such that the oxygen production control engine 404 receives that other sensor information through the wound oxygen supply system communication subsystem 412.

As discussed above, the other sensor subsystems in the wound oxygen supply systems 100 and 200 may include the pressure sensor subsystem 122b and 214b, respective which may operate to provide pressure information to the oxygen production control engine 104 and 404, respectively, that is indicative of a pressure in the restricted airflow enclosure provided by the bandage subsystem 700 and bandage subsystem/wound oxygen supply system 800, respectively. As discussed above, the other sensor subsystems in the wound oxygen supply systems 100 and 200 may include the flow rate sensor subsystem which may operate to provide flow rate information to the oxygen production control engine 104 and 404, respectively, that is indicative of a flow rate of oxygen to the restricted airflow enclosure provided by the bandage subsystem 700 and bandage subsystem/wound oxygen supply system 800, respectively. As also discussed above, the other sensor subsystems in the wound oxygen supply systems 100 and 200 may include the temperature sensor subsystems which may operate to provide temperature information to the oxygen production control engine 104 and 404, respectively, that is indicative of a temperature in the restricted airflow enclosure provided by the bandage subsystem 700 and bandage subsystem/wound oxygen supply system 800, respectively. As also discussed above, the other sensor subsystems in the wound oxygen supply systems 100 and 200 may include the pH sensor subsystems which may operate to provide pH information to the oxygen production control engine 104 and 404, respectively, that is indicative of a pH in the restricted airflow enclosure provided by the bandage subsystem 700 and bandage subsystem/wound oxygen supply system 800, respectively. As also discussed above, the other sensor subsystems in the wound oxygen supply systems 100 and 200 may include the perfusion sensor subsystems which may operate to provide perfusion information to the oxygen production control engine 104 and 404, respectively, that is indicative of perfusion in the restricted airflow enclosure provided by the bandage subsystem 700 and bandage subsystem/wound oxygen supply system 800, respectively.

The method 500 then proceeds to optional block 512 where the other sensor information may be used to control the power provided to the oxygen production subsystem. In an embodiment, with reference to the bandage subsystem 700 and wound oxygen supply system 100 discussed above, at block 512 the oxygen production control engine 104 may use the other sensor information received from the other sensor subsystem(s) to control the power provided by the power subsystem 112 to the oxygen production subsystem 116. In a specific example, at block 512 the wound oxygen supply systems 100 and/or 200 may provide the humidity sensor subsystem and its functionality described above to cause the oxygen production subsystem to generate a desired oxygen flow to the restricted airflow enclosure, while using the pressure sensor subsystem to determine when the pressure in restricted airflow enclosure reaches a maximum level and, in response, prevent the oxygen production subsystem from generating oxygen until that pressure falls below the maximum level. The use of the humidity sensor subsystem and pressure sensor subsystem in place of conventional flow sensor subsystem/pressure sensor subsystem devices provides for a reduced chassis size and ability to address humidity related issues with the oxygen production subsystem, while still enabling precise control of the oxygen supply to the restricted airflow enclosure adjacent the wound.

However, at block 512 the oxygen production control engine 104 may also utilize any of the pressure information, flow rate information, temperature information, pH information, and/or perfusion information along with the humidity information to determine a power amount to provide to the oxygen production subsystem 116, and then cause the power subsystem 112 to provide a particular power amount to the oxygen production subsystem 116 by, for example, sending an instruction to the power subsystem 112 to transmit that power amount to the oxygen production subsystem 116. However, in other embodiments, the other sensor information received at block 510 may not be used to control power provided to the oxygen production subsystem 116, but rather may instead be used to monitor the wound 602 or perform other functionality. For example, other sensor information such as pressure information may be utilized to ensure the pressure in the restricted airflow enclosure is at a desired level, to verify that the patient 600 is using the wound oxygen supply system, or to perform other functions that would be apparent to one of skill in the art in possession of the present disclosure.

In another embodiment, with reference to the bandage subsystem/wound oxygen supply system 800 and the control device 400 discussed above, at block 506 the oxygen production control engine 404 uses the other sensor information received from the other sensor subsystem(s) to control the power provided by the power subsystem 206 to the oxygen production subsystem 208. As such, at block 512 the oxygen production control engine 104 may utilize any of the pressure information, flow rate information, temperature information, pH information, and/or perfusion information along with the humidity information to determine a power amount to provide to the oxygen production subsystem 208, and then transmit an instruction via the wound oxygen supply system communication subsystem 412 to the control device communication subsystem 204 in the wound oxygen supply system 200, and the control device communication subsystem 204 may, in response, cause the power subsystem 206 to provide that particular power amount to the oxygen production subsystem 208 by, for example, forwarding that instruction to the power subsystem 206 to transmit that power amount to the oxygen production subsystem 208. However, in other embodiments, the other sensor information received at block 510 may not be used to control power provided to the oxygen production subsystem 208, but rather may instead be used to monitor the wound 602. The method 500 then proceeds to optional block 514 where the oxygen production subsystem may produce the oxygen flow using the power provided according to the other sensor information in substantially the same manner as described above with reference to block 508.

Figure 11:
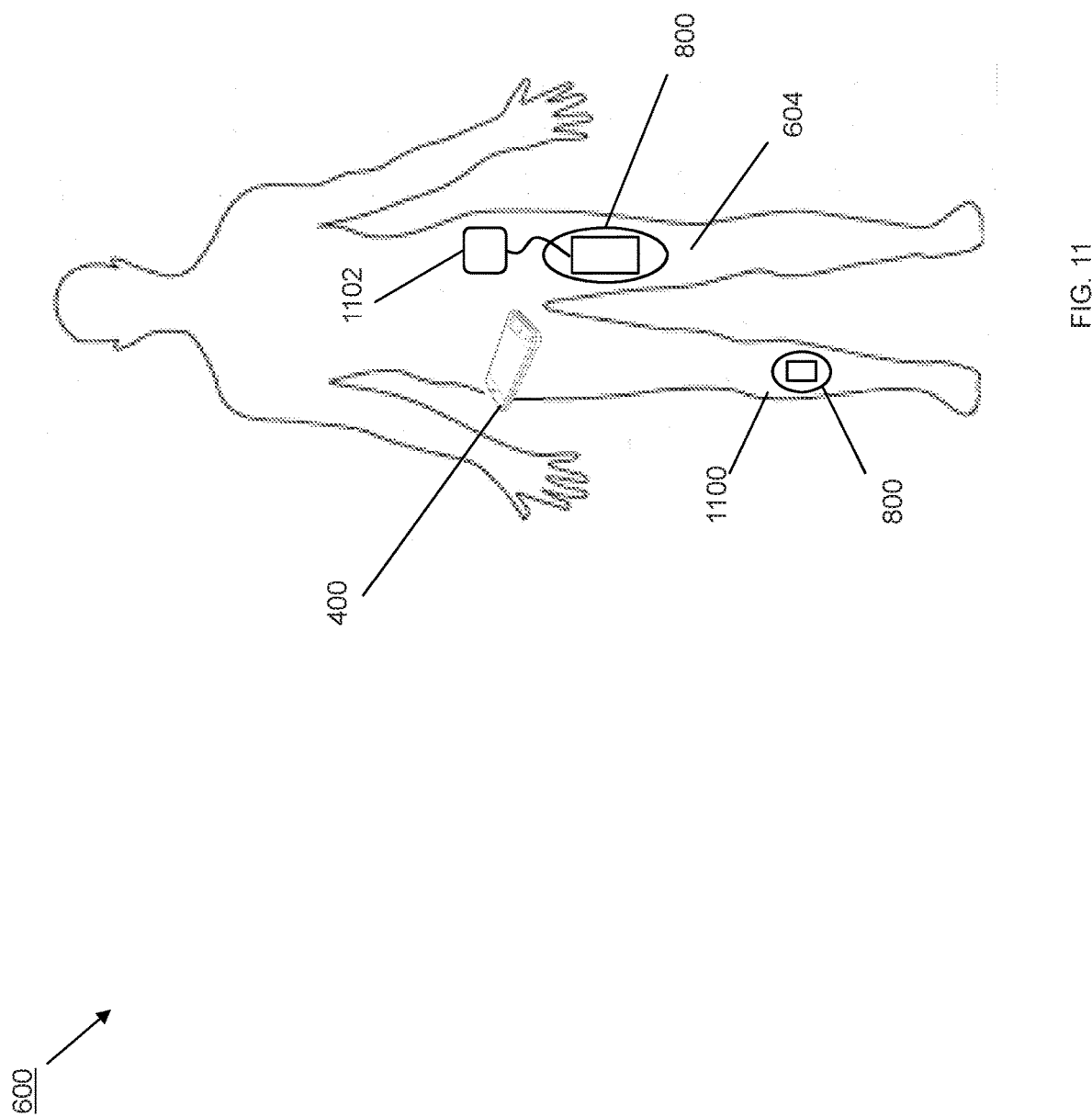
FIG. 11 is a schematic view illustrating an embodiment of the patient of FIG. 6 with additional wounds, and utilizing additional wound oxygen supply systems and bandage subsystems of FIG. 9A and the control device of FIGS. 4A-4B.

The method 500 may then return to block 504 where the humidity information is received that is indicative of the humidity experienced by the oxygen production subsystem in the wound oxygen supply system, and the method 500 loops back through blocks 504-508, and in some cases optional blocks 510-514, to provide the oxygen flow to the restricted airflow enclosure. As such, oxygen may be provided to a wound and, in some cases, continuously varied to enhance the healing of that wound. Furthermore, combinations of the teachings above may be provided to enhance the healing of more than one wound. For example, FIG. 11 illustrates the patient 600 of FIG. 6 with the wound 602 on the leg 604, and including a second, smaller wound on a leg 1100 as well. In the illustrated embodiment, an embodiment of the bandage subsystem/wound oxygen supply system 800 is provided on the relatively larger wound 602, with a connection (via a power connector provided by the power subsystem 206) to an external portable power source 1102 (e.g., a battery, solar energy collecting clothing, etc.) that is provided to produce an increased level of oxygen generation by the wound oxygen supply system 200 for the larger wound 602, and that may be worn by the patient 600 (e.g., on a belt, in a pocket, etc.) In addition, an embodiment of the bandage subsystem/wound oxygen supply system 800 is provided on the relatively smaller wound on the leg 1100, and which includes sufficient internal power (e.g., via an internal battery) to provide sufficient oxygen generation by the wound oxygen supply system 200 for the smaller wound on the leg 1100. As illustrated, the control device 400 may provide for control of the multiple wound oxygen supply systems utilized by the patient 600 in substantially the same manner as described above.

Furthermore, FIG. 12 illustrates how a single wound oxygen supply system 100 may be utilized to treat multiple wounds on a patient, as discussed above. For example, in FIG. 12, a first bandage subsystem 700 has been placed on a wound on the shoulder of the patient 600, while a second bandage subsystem 700 has been placed on a wound on the leg 604 of the patient 600, and each of those first and second bandage subsystems 700 have been coupled to oxygen outlet(s) on the chassis 102 of the wound oxygen supply system 100. As such, the chassis 102 may house multiple oxygen production subsystems, each with a dedicated oxygen outlet, sensor subsystems, and/or other features discussed above, and with each configured to supply oxygen to a wound in substantially the same manner as discussed above. Furthermore, in some embodiments, a single oxygen production subsystem may be coupled to a single oxygen outlet, with a single set of sensor subsystems, and may be coupled to multiple wounds (e.g., via multiple tubings branched tubing, etc.) to supply oxygen to those multiple wounds in substantially the same manner as discussed above. Thus, one of skill in the art in possession of the present disclosure will recognize that a variety of modifications may be made to the systems and methods of the present disclosure in order to allow multiple wounds to be treated while remaining within the scope of the present disclosure.

In addition to the functionality described above, the wound oxygen supply systems 100 and 200 may operate to receive a variety of input information via their input subsystems (e.g., the input subsystem 110 on the wound oxygen supply system 100, the input subsystem 410 on the control device 400 that may utilize the wound oxygen supply system communication subsystem 412 to transmit input information to the wound oxygen supply system 200, etc.) and/or display a variety of display information via their display subsystems (e.g., the display subsystem 108 on the wound oxygen supply system 100, the display subsystem 408 on the control device 400 that may utilize the wound oxygen supply system communication subsystem 412 to receive display information from the wound oxygen supply system 200, etc.) For example, input information may include control instructions to adjust a desired oxygen flow rate produced by the oxygen production subsystems 116/208, cause software for the wound oxygen supply systems 100 and/or 200 to be updated, and/or any of a variety of other input information that would be apparent to one of skill in the art in possession of the present disclosure. In another example, display information may include the display of a current oxygen flow rate produced by the oxygen production subsystems 116/208, the status of a software update for the wound oxygen supply systems 100 and/or 200, and/or any of a variety of other display information that would be apparent to one of skill in the art in possession of the present disclosure.

Furthermore, the communication subsystems provided in the wound oxygen supply systems 100 and/or 200 (and or in association with the wound oxygen supply system 200 in the case of the control device 400) may be utilized to communicate with other entities as well. For example, the wound oxygen supply system 100 may utilize its communication subsystem to download data (e.g., operating instructions) for use in at least one subsequent operation of the wound oxygen supply system 100, and/or upload data (e.g., previously generated data) that describes previous operation of the wound oxygen supply system 100. Similarly, the control device 400 may utilize its communication subsystem to download data (e.g., operating instructions) for use in at least one subsequent operation of the wound oxygen supply system 200, and in some cases provide that data to the wound oxygen supply system 200, and/or upload data (e.g., previously generated data) that describes previous operation of the wound oxygen supply system 100. As such, data generated by the wound oxygen supply system and describing the use of that wound oxygen supply system may be saved and reported back to a caregiver or other entity, and a caregiver or other entity may remotely control the operation of the wound oxygen supply systems to remotely care for the patient.

Thus, systems and methods have been described that monitor the humidity experienced by an oxygen production subsystem and use that humidity level to control the power provided by a power subsystem to the oxygen production subsystem in order to control an oxygen flow that is created by the oxygen production subsystem and provided through an oxygen outlet to a restricted airflow enclosure adjacent a wound. The systems and methods of the present disclosure allow for the conventional flow sensor subsystems utilized in the wound treatment systems discussed above to be replaced with the humidity sensor subsystem described herein, providing a reduction in the cost and size of the wound oxygen supply system, while still enabling low dose tissue oxygenation and continuous oxygen adjustability to a wound site, preventing deficient wound site oxygen supply that conventional wound treatment systems experience in low humidity environments, and preventing problems associated with increases in power that are provided to the oxygen production subsystem to address the reduced oxygen production capabilities that result from such low humidity environments Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A wound oxygen supply system, comprising:
a chassis that defines an oxygen outlet;
an oxygen production subsystem that is included in the chassis and coupled to the oxygen outlet; and
a control subsystem that is coupled to the oxygen production subsystem and that includes an oxygen production control database that includes oxygen production control data that associates, for each of a plurality of different power amounts, oxygen outputs of the oxygen production subsystem over a range of different humidity levels, wherein the control subsystem is configured to:
  receive humidity information that is indicative of a humidity experienced by the oxygen production subsystem;
  retrieve, from the oxygen production control database using the humidity information, first oxygen production control data that includes a power amount that is configured to cause the oxygen production subsystem to produce a desired oxygen output; and cause the power amount to be provided to the oxygen production subsystem in order to cause the oxygen production subsystem to produce the desired oxygen output that is provided through the oxygen outlet to a restricted airflow enclosure.

2. The system of claim 1, further comprising:

a power subsystem that is located in the chassis, coupled to the oxygen production subsystem and the control subsystem, and configured to provide the power to the oxygen production subsystem.

3. The system of claim 1, further comprising:

a pressure sensor that is located in the chassis and configured to provide pressure information to the control subsystem.

4. The system of claim 1, wherein the oxygen production control database is included in the chassis.

5. The system of claim 1, further comprising:

a display subsystem that is included on the chassis and coupled to the control subsystem; and an input subsystem that is included on the chassis and coupled to the control subsystem, wherein the control subsystem is configured to:

provide, for display on the display subsystem, display information; and receive, from the input subsystem, input information.

6. The system of claim 5, wherein the input subsystem includes a touch screen input subsystem that is integrated with the display subsystem.

7. The system of claim 1, further comprising:

a data communication subsystem that is coupled to the control subsystem, wherein the control subsystem is configured to perform at least one of:

downloading, using the data communication subsystem, data for use in at least one subsequent operation of the system; and uploading, using the data communication subsystem, data generated during at least one previous operation of the system.

8. A method for supplying oxygen to a wound, comprising:

receiving, by a control subsystem from a humidity sensor, humidity information that is indicative of a humidity experienced by an oxygen production subsystem that is coupled to a restricted airflow enclosure;

accessing, by the control subsystem, an oxygen production control database that is included in the control subsystem and that includes oxygen production control data that associates, for each of a plurality of different power amounts, oxygen outputs of the oxygen production subsystem over a range of different humidity levels;

retrieving, by the control subsystem from the oxygen production control database using the humidity information, first oxygen production control data that includes a power amount that is configured to cause the oxygen production subsystem to produce a desired oxygen output;

causing, by the control subsystem, the power amount to be provided to the oxygen production subsystem; and creating, by the oxygen production subsystem using the power amount, the desired oxygen output such that oxygen is provided to the restricted airflow enclosure.

9. The method of claim 8, further comprising:

providing, by a power subsystem to the oxygen production subsystem, the power amount.

10. The method of claim 8, wherein the oxygen production control database is included in a chassis that houses the control subsystem.

11. The method of claim 8, further comprising:

providing, by the control subsystem for display on a display subsystem, display information; and receiving, by the control subsystem from an input subsystem, input information.

12. The method of claim 11, wherein the input subsystem includes a touch screen input subsystem that is integrated with the display subsystem.

13. The method of claim 8, further comprising:

downloading, by the control subsystem using a data communication subsystem, data for use in subsequently treating at least one wound; and uploading, by the control subsystem using the data communication subsystem, data generated during at least one previous wound treatment.

14. A wound oxygen supply system, comprising:

a processing system; and a memory system that is coupled to the processing system and that includes instructions that, when executed by the processing system, cause the processing system to perform operations including:

receiving humidity information that is indicative of a humidity experienced by an oxygen production subsystem;

accessing an oxygen production control database that includes oxygen production control data that associates, for each of a plurality of different power amounts, oxygen outputs of the oxygen production subsystem over a range of different humidity levels;

retrieving, from the oxygen production control database using the humidity information, first oxygen production control data that includes a power amount that is configured to cause the oxygen production subsystem to produce a desired oxygen output; and causing the power amount to be provided to the oxygen production subsystem in order to cause the oxygen production subsystem to produce the desired oxygen output that is provided to a restricted airflow enclosure.

15. The wound oxygen supply system of claim 14, wherein the oxygen production control database is included in a chassis that houses the processing system and the memory system.

16. The wound oxygen supply system of claim 14, wherein the operations further comprise:

providing, for display on a display subsystem, display information.

17. The wound oxygen supply system of claim 16, wherein the operations further comprise:

receiving, from an input subsystem, input information.

18. The wound oxygen supply system of claim 17, wherein the input subsystem includes a touch screen input subsystem that is integrated with the display subsystem.

19. The wound oxygen supply system of claim 14, wherein the operations further comprise:

downloading, using a data communication subsystem, data for use in at least one subsequent operation of the wound oxygen supply system.

20. The wound oxygen supply system of claim 14, wherein the operations further comprise:

uploading, using a data communication subsystem, data generated during at least one previous operation of the wound oxygen supply system.

* * * * *